(12) United States Patent
Feola et al.

(10) Patent No.: US 7,989,186 B2
(45) Date of Patent: Aug. 2, 2011

(54) COMPOSITIONS AND METHODS FOR DETECTING CRYPTOCOCCUS NEOFORMANS

(75) Inventors: Melanie Feola, Cherry Hill, NJ (US);
Martin Adelson, Belle Mead, NJ (US);
Eli Mordechai, Robbinsville, NJ (US);
John Entwistle, Christiansburg, VA (US)

(73) Assignee: Medical Diagnostic Laboratories, LLC, Hamilton, NJ (US)

( * ) Notice: Subject to any disclaimer, the term of this patent is extended or adjusted under 35 U.S.C. 154(b) by 401 days.

(21) Appl. No.: 12/214,317

(22) Filed: Jun. 18, 2008

(65) Prior Publication Data
US 2009/0246767 A1  Oct. 1, 2009

Related U.S. Application Data

(60) Provisional application No. 60/936,628, filed on Jun. 20, 2007.

(51) Int. Cl.
*C12P 19/34* (2006.01)
(52) U.S. Cl. .................................... 435/91.2
(58) Field of Classification Search .......... 435/91.2
See application file for complete search history.

(56) References Cited

U.S. PATENT DOCUMENTS

| | | | |
|---|---|---|---|
| 5,464,743 A | 11/1995 | Weisburg | |
| 5,580,971 A | 12/1996 | Mitsuhashi | |
| 5,707,802 A | 1/1998 | Sandhu | |
| 5,763,163 A | 6/1998 | Milliman | |
| 5,763,169 A | 6/1998 | Sandhu | |
| 5,919,617 A | 7/1999 | Bhattacharjee | |
| 6,180,339 B1 | 1/2001 | Sandhu | |
| 2003/0228599 A1 | 12/2003 | Straus | |

OTHER PUBLICATIONS

Lfotus et al., Science vol. 307, pp. 1321-1324, Feb. 2005.*
Chomczynski P. et al. Single-step method of RNA isolation by acid guanidinium thionycate-phenol-chloroform extraction. Analytical Biochem. 162 ,156-159, 1987.
King J. W., Dasgupta A.Cryptococcosis. emedicine. Jun. 2007.
Hybridization Analysis of DNA Blots.Current Protocols in Molecular Biology. Wiley and Sons. 1993. 2.10.1-2.10.16.
Hybridization with Radioactive Probes.Current Protocols in Molecular Biology. Wiley and Sons.1993. 6.3.1-6.3.6.
Vernon, V. et al., Diagn. Microbiol. Infect. Dis., 65: 69-72, 2009.
Lau, A. et al., J. Clin. Microbiol., 46(9): 3021-3027, 2008.
Makimura, K. et al., J. Med. Microbiol., 40: 358-364, 1994.
Bialek, R. et al., Clin. Diagn. Lab. Immunol., 9(2): 461-469, 2002.
Paschoal, R. C. et al., Rev. Inst. Med. Trop. S. Paulo., 46(4): 203-207, 2004.

* cited by examiner

*Primary Examiner* — Gary Benzion
*Assistant Examiner* — Cynthia Wilder
(74) *Attorney, Agent, or Firm* — Siu K. Lo, JD; Michael T. Barber

(57) ABSTRACT

Disclosed are oligonucleotides useful in methods for determining whether a sample contains *Cryptococcus neoformans*, a causative agent for human cryptococcosis. These oligonucleotides, which have nucleotide sequences derived from a coding segment of the gene encoding the fungal specific transcription factor gene in *Cryptococcus neoformans*, are useful as forward and reverse primers for a polymerase chain reaction using nucleic acids from a biological sample as templates, and as probes for detecting any resultant amplicon. Detection of an amplicon indicates the sample contains *Cryptococcus neoformans*. Real-time PCR and detection using florescence resonance energy transfer is disclosed.

8 Claims, 5 Drawing Sheets

Figure 1

```
1     taaccccta acccctctaac cccctaaccc cctaacccc taacccccta accccctaac
61    cccctaaccc ctaaccccct aagttagcga cgaggagtgg aggttgaatg atcttaaaag
121   gtgttttta agtagttttt aattcgggta gcatacacga caacccaata agttaaacaa
181   cgcaaacatg caacctctat aaccctcgct cattcaacaa tttcgaggtg ttttggacaa
241   gtagacggtt tgagaagact aagctggaca aaagatgaac attgttagcc agcggcacgt
301   ctcgccagcg tgatggtaaa cttgcttaaa cattaaacat tacaaggatt tcatgtgaaa
361   ctattgtgag gggcaaaaaa gctatcaaat atactctgct ggtctgcatc caaaggccag
421   taattgataa gatcatctgg aagagtgaag accgtatcat cataacctgt ctgacttatg
481   gcttcaaatg caggctgaga atcgagtta ctgtctaatg aggaagcaaa tggcaattca
541   ggaccacttt cgtccgctgg ttttctgca cgactgacaa cagcaatttt gggcagctgt
601   ggaccgttga tttgtggatt aggctgtggt gcagtgtttg tcctcgctcg agagggtag
661   gagactgtgg gcgattcgcc ttgaaaaatg tgatggtccg gttttcggtt gtcaaccgtt
721   gactgcatga agagatcgat tcgggcgata tgcttaagaa gccgctcgct gatccctcct
781   ccggggataa aaggagtctc gaggcaggca agtaagtttg cgaatgacaa actgttcggt
841   cagctttgtt aggacaataa gcgcagttgg acagacagga gggcagctta caggatctgg
901   cggatatgaa ggtacgtgct gatggtcaaa ggaccctgca ccacgctccc caaaagactg
961   ccgactgccg atagctgatg aagctataaa ggaaggtggt cagcaacagg tgaagcgctc
1021  gctctgatga aggcaaaccg acgtacgaat ggcgcgctga tcaactgcat gtacgctgtg
```

Cneo F 1
                                                            ───────────▶

```
1081  ggtatattcg ccagaacatc cagcagctcg cctgcgatct GACATCGATC TGCCATACTC
```

Cneo Probe
                                      ◀──────▶

```
1141  ATCGgctggC AACAAGCGAT TGCCATCCGA ACAGCCTTtc ctctgtcagc aacttgagcc
```

Cneo R 1
                                                            ◀───────────

```
1201  cggattgcaa aggtatactt tcggcatCAA CTGACCTGTA GTGTGACGCtcaaattcgcc
1261  gcttgaaagc tacagacatt gtcgacaaag tccccgtca atggcttcgt ctccttgaac
1321  accgatggca acgcgtcgta tctatatctg atgactggcc aagactcgct gacggaaagc
1381  gggggacggc cgaatggact tggtagatct ggaggcttat gtggggcggc ccgttgattt
1441  tgatacgctg cagcatccat tatctcctcc atggcgcggt acaaatcggt cacggtattc
1501  caccccctgta tccagttcac ggtatccagc tcgcctacca acgtaggtga aagagataag
1561  gcgtcgtcca gtcggtgatc tgggtatgag acgaagcttt ggcatcttcg atgacggatc
1621  acaccgcccc aaacggatga cgcgaagaca tcgagcgtat atattgacca gtactactcc
1681  gtccgtcacc attttcccca cggaagcaag acatatagat acgcaccaaa cacctcctct
1741  cctgtacttc ccattttccc agccctgcg gccactgtga ctcgtcgtga aacgccaatt
1801  gcgccgacat cccatgatac tgcccgagca tgatctgcaa ttggtcgaaa tccccattct
1861  gtatacccaa aatcgccagt aaagctgttg ctctcagatc gtcgaattcc ggtccgctac
1921  ctgaggcgcg cgaggatatg ctggacaaag cggcgcttcg cagaccgtgg acattcgata
1981  ttatcgctat atcggtgatt ccgcttgagt ctgactggct ggaaggtggg gaccagacct
2041  tgagtagctc gctacatgct ccatcgcgca gacgcgctgc tgccacggca cagacggcca
2101  aaacggatgc ttggaaggat ctatcattat cctgacggcg cgccttgacg tgattaatga
2161  aggttggcca gtgaaagaaa caatacctgc ggaacattca gctgatgatc atcagttggg
2221  cagtcctacga agttcactg gatacgcgt catccggtac acctccgcaa gctgcagggt
2281  ggtgtcaaga tctatgttgt tggtagctat ccattcgctg gtattgcttg ctcgaatgga
2341  agacggagct ggctgtagcg gtgcatttt gggaggagcc tggacagggc attagcaaaa
2401  tgcaacctgg aatgacttct taacccaccc ctcttcttcc ctgaggtcga tcgtacgtgc
2461  atttttgccc ataatcaata cacggctgac atagtggtgg ggcctctgaa ggcgagcact
2521  gatagactga tcaatcgaga tccacagctc caaatcgata atttcctcac cttattcccg
2581  agtttatggc atctatcgca ggctctctgg atgacatcag tgcagggatc gccggaggat
2641  aacagtaccc actgagaccc gttttctctt ggaacccaac atgattgatc agtcaagtag
2701  agtttaggat aatcatcaaa gatctggtaa taatcggcaa acaaataaga tgttttttg
```

COMPOSITIONS AND METHODS FOR DETECTING CRYPTOCOCCUS NEOFORMANS

CROSS-REFERENCE TO RELATED APPLICATION

The present application claims the benefit of priority to U.S. Provisional Application No. 60/936,628 filed Jun. 20, 2007, the entire disclosure of which is hereby incorporated by reference in its entirety.

FIELD OF THE INVENTION

Example embodiments are generally directed to sensitive and specific PCR assays for detecting *Cryptococcus neoformans*. Example embodiments also provide forward and reverse primers to target against the fungal specific transcription factor gene in *Cryptococcus neoformans*, as well as hybridization probes containing a fluorescent moiety, such as fluorescein, so as to render a real-time PCR assay to detect the presence of *Cryptococcus neoformans*. Other example embodiments may include assays employing conventional PCR to detect the presence of *Cryptococcus neoformans*.

BACKGROUND

*Cryptococcus neoformans* is an encapsulated fungus, and is the etiological agent of human cryptococcosis. This fungal pathogen represents an opportunistic organism and mainly infects immuno-compromised and immuno-competent individuals. There are roughly 0.4-1.3 cases per 100,000 per year in the general population. Among AIDS patients, however, the annual incidence is 200-700 cases per 100,000. The species *Cryptococcus neoformans* is composed of three variants; namely *Cryptococcus neoformans* v. *gattii*, *Cryptococcus neoformans* v. *grubii*, and *Cryptococcus neoformans* v. *neoformans*. The *grubii* and *neoformans* variants have a worldwide distribution and are often found in soil which has been contaminated by bird excrement. Infections are typically acquired by inhalation of the desiccated fungal cells known as basidiospores. Primary infection with *Cryptococcus neoformans* is thought to be common early in life where the disease can either lie dormant in the lungs or disseminate to the central nervous system. With pulmonary disease, the infection may be acute or chronic. If the fungal pathogen is able to disseminate, infection can present itself as meninogencephalitis, cutaneous lesions, and other inflammatory symptoms.

Conventional detection methods for *Cryptococcus neoformans* include culture on fungal media, colony morphology and nutritional characteristics. Fungi (such as *Cryptococcus neoformans*) may take 2-3 days or even weeks to grow in culture. This makes timely identification difficult and greatly impairs efficient treatment where rapid identification of fungal genus/species is required. Most of these methods are either time-consuming, laborious, or provide inconclusive results.

U.S. Pat. Nos. 5,464,743, 5,580,971, 5,763,163, 5,763,169, 5,707,802, and 6,180,339 disclose detection of fungus including *Cryptococcus neoformans* using a PCR assay to detect ribosomal RNA (rRNA). The designed probes are targeted against 28S rRNA. U.S. Pat. No. 6,180,339 describes amplification of a 401 bp fragment spanning the large subunit rRNA/intergenic spacer region. This PCR-based assay has limitation because of its lack of specificity. Multiple probes may be required to distinguish among fungal species.

U.S. Pat. No. 5,919,617 discloses, besides immunological means, the use of primer pairs to amplify the saccharopine dehydrogenase gene to detect *Candida albicans*.

SUMMARY

There is a continuing need for a specific, rapid and sensitive PCR assay to detect the presence of *Cryptococcus neoformans* in a biological sample from a patient for early diagnosis and treatment. More specifically, there is a need for a highly specific PCR assay to distinguish *Cryptococcus neoformans* from other microorganisms. Disclosed herein are oligonucleotide primers and hybridization probes for use in polymerase chain reaction ("PCR") methods, such as real-time PCR methods, for specifically detecting *Cryptococcus neoformans* in a patient. Also disclosed are sensitive and specific PCR assays for detecting *Cryptococcus neoformans*. Further disclosed are kits that include such oligonucleotide primers and/or hybridization probes.

Provided herein are isolated oligonucleotide primers having about 15-25 nucleotides in length, which are capable of annealing under PCR conditions (such as real-time PCR conditions) to a segment of the fungal specific transcription factor gene of *Cryptococcus neoformans*. The segment of the fungal specific transcription factor gene may, for example, have a consensus sequence that has at least a 99%, 95% or 90% identity to the following sequences: (a) nucleotides 1121-1144 of SEQ ID NO: 1, (b) nucleotides 1480-1499 of SEQ ID NO: 1, (c) nucleotides 2105-2124 of SEQ ID NO: 1, (d) nucleotides 1512-1533 of SEQ ID NO: 2, (e) nucleotides 1165-1184 of SEQ ID NO: 2, and (f) nucleotides 508-527 of SEQ ID NO: 2.

Example embodiments provide an isolated oligonucleotide primer consisting essentially of nucleotide sequence set forth in SEQ ID NO: 3, the nucleotide sequence set forth in SEQ ID NO: 4, the nucleotide sequence set forth in SEQ ID NO: 6, the nucleotide sequence set forth in SEQ ID NO: 7, the nucleotide sequence set forth in SEQ ID NO: 8, and the nucleotide sequence set forth in SEQ ID NO: 9.

The term "consisting essentially of," throughout this application is intended to encompass sequences having at least 99%, 95% or 90% identity to those identified herein. Thus, the following embodiments are examples thereof.

Example embodiments provide an isolated oligonucleotide, which has at least about 99% identity to a nucleotide sequence of: (a) nucleotides 1121-1144 of SEQ ID NO: 1, (b) nucleotides 1480-1499 of SEQ ID NO: 1, (c) nucleotides 2105-2124 of SEQ ID NO: 1, (d) nucleotides 1512-1533 of SEQ ID NO: 2, (e) nucleotides 1165-1184 of SEQ ID NO: 2, and (f) nucleotides 508-527 of SEQ ID NO: 2.

Further example embodiments provide an isolated oligonucleotide, which has at least about 95% identity to a nucleotide sequence of: (a) nucleotides 1121-1144 of SEQ ID NO: 1, (b) nucleotides 1480-1499 of SEQ ID NO: 1, (c) nucleotides 2105-2124 of SEQ ID NO: 1, (d) nucleotides 1512-1533 of SEQ ID NO: 2, (e) nucleotides 1165-1184 of SEQ ID NO: 2, and (f) nucleotides 508-527 of SEQ ID NO: 2.

Further example embodiments provide an isolated oligonucleotide, which has at least about 90% identity to a nucleotide sequence of: (a) nucleotides 1121-1144 of SEQ ID NO: 1, (b) nucleotides 1480-1499 of SEQ ID NO: 1, (c) nucleotides 2105-2124 of SEQ ID NO: 1, (d) nucleotides 1512-1533 of SEQ ID NO: 2, (e) nucleotides 1165-1184 of SEQ ID NO: 2, and (f) nucleotides 508-527 of SEQ ID NO: 2.

Other example embodiments provide an isolated hybridization probe. The hybridization probe has a nucleotide sequence consisting essentially of a sequence complementary to consensus nucleotide sequence of nucleotides 1150-1178 of SEQ ID NO: 1 or nucleotides 1583-1611 of SEQ ID NO: 2. The hybridization probe may include a fluorescent reporter group, molecule or moiety, such as a fluorescein moiety, e.g., at its 5' or 3' end. According to example embodiments, the fluorescent moiety may be a 6-carboxy-fluorescein.

In example embodiments, the hybridization probe may have the nucleotide sequence set forth in SEQ ID NO: 5.

According to example embodiments, the hybridization probe may have at least about 99%, 95% or 90% identity to a nucleotide sequence complementary to consensus nucleotide sequence of nucleotides 1150-1178 of SEQ ID NO: 1 or nucleotides 1583-1161 of SEQ ID NO: 2.

According to non-limiting example embodiments, provided are methods of detecting the presence of *Cryptococcus neoformans* in a biological sample. Such methods include:

(a) mixing (i) extracted DNA obtained from said biological sample, and (ii) a primer pair containing a forward primer and a reverse primer, which target fungal specific transcription factor gene of *Cryptococcus neoformans*, (b) amplifying, in a PCR reaction, under conditions to allow production of an amplicon; and (c) detecting the presence or absence of *Cryptococcus neoformans*, in the sample.

According to further non-limiting example embodiments, methods are provided for detecting the presence of *Cryptococcus neoformans* in a biological sample using real-time PCR. Such methods include:

(a) mixing (i) extracted DNA obtained from the biological sample, (ii) a primer pair containing a forward primer and a reverse primer, that target fungal specific transcription factor gene of *Cryptococcus neoformans*, and (iii) a hybridization probe that targets fungal specific transcription factor gene of *Cryptococcus neoformans* in a PCR vessel, wherein the hybridization probe includes a fluorescent moiety;

(b) amplifying, in a real-time PCR reaction, under conditions to allow production of an amplicon; and (c) detecting the presence or absence of *Cryptococcus neoformans*, by detecting the presence or absence of a fluorescent signal resulting from the formation of the amplicon, wherein the presence of a fluorescent signal is indicative of the presence of *Cryptococcus neoformans*.

According to non-limiting example embodiments, the forward primer consists essentially of nucleotide sequence 1121-1144 set forth in SEQ ID NO.: 1, nucleotide sequence 1480-1499 set forth in SEQ ID NO: 1, or nucleotide sequence 2105-2124 set forth in SEQ ID NO: 1, the reverse primer consists essentially of nucleotide sequence 1512-1533 set forth in SEQ ID NO: 2, nucleotide sequence 1165-1184 set forth in SEQ ID NO: 2, or nucleotide sequence 508-527 set forth in SEQ ID NO: 2, and the hybridization probe consists essentially of nucleotide sequence 1150-1178 of SEQ ID NO: 1 or nucleotide sequence 1583-1611 of SEQ ID NO: 2.

According to further non-limiting example embodiments, the forward primer has at least 99%, 95% or 90% identity to a nucleotide sequence 1121-1144 set forth in SEQ ID NO: 1. nucleotide sequence 1480-1499 set forth in SEQ ID NO.: 1, or nucleotide sequence 2105-2124 in SEQ ID NO: 1. The reverse primer has at least 90%, 95% or 99% identity to a nucleotide sequence 1512-1533 set forth in SEQ ID NO: 2, nucleotide sequence 1165-1184 set forth in SEQ ID NO.: 2, or nucleotide sequence 508-527 set forth in SEQ ID NO: 2, and the hybridization probe has at least 90%, 95% or 99% identity to a nucleotide sequence 1150-1178 of SEQ ID NO: 1 or nucleotide sequence 1583-1611 of SEQ ID NO: 2.

According to example embodiments, the forward primer consists essentially of a nucleotide sequence set forth in SEQ ID NO: 3, and a reverse primer consists essentially of a nucleotide sequence set forth in SEQ ID NO: 4. According to other example embodiments, the forward primer consists essentially of a nucleotide sequence set forth in SEQ ID NO: 6, and a reverse primer consists essentially of a nucleotide sequence set forth in SEQ ID NO: 7. According to other example embodiments, the forward primer consists essentially of a nucleotide sequence set forth in SEQ ID NO: 8, and a reverse primer consists essentially of a nucleotide sequence set forth in SEQ ID NO: 9.

According to example embodiments, the fluorescent moiety may be a fluorescein, and more particularly, 6-carboxyfluorescein, which may be attached at a 5'- or 3' end of the hybridization probe.

In other example embodiments kits are provided for PCR for detection of *Cryptococcus neoformans*. Example kits may include the following:

(a) a forward primer that anneals to a *Cryptococcus neoformans* consensus sequence consisting essentially of nucleotides 1121-1144 of SEQ ID NO: 1;

(b) a reverse primer that anneals to a *Cryptococcus neoformans* consensus sequence consisting essentially of nucleotides 1512-1533 of SEQ ID NO: 2; and (c) instructions for using said forward primer and reverse primer in performing PCR to detect a presence of *Cryptococcus neoformans* in a sample.

Other example kits may include the following:

(a) a forward primer that anneals to a *Cryptococcus neoformans* consensus sequence consisting essentially of nucleotides 1480-1499 of SEQ ID NO: 1;

(b) a reverse primer that anneals to a *Cryptococcus neoformans* consensus sequence consisting essentially of nucleotides 1165-1184 of SEQ ID NO: 2; and (c) instructions for using said forward primer and reverse primer in performing PCR to detect a presence of *Cryptococcus neoformans* in a sample.

Other example kits may include the following:

(a) a forward primer that anneals to a *Cryptococcus neoformans* consensus sequence consisting essentially of nucleotides 2105-2124 of SEQ ID NO: 1;

(b) a reverse primer that anneals to a *Cryptococcus neoformans* consensus sequence consisting essentially of nucleotides 508-527 of SEQ ID NO: 2; and (c) instructions for using said forward primer and reverse primer in performing PCR to detect a presence of *Cryptococcus neoformans* in a sample.

Kits are also provided for real-time PCR in particular. According to such embodiments, the kits above may further include a hybridization probe having a nucleotide sequence consisting essentially of a sequence set forth in SEQ ID NO: 5, wherein the probe includes a fluorescent moiety; and the instructions are instructions for using the forward primer, reverse primer and hybridization probe in performing real-time PCR in detecting a presence of *Cryptococcus neoformans* in a sample.

Thus, according to example embodiments, kits are provided for real-time PCR for detection of *Cryptococcus neoformans*, which include the following:

(a) a forward primer that anneals to a *Cryptococcus neoformans* consensus sequence consisting essentially of nucleotides 1121-1144 of SEQ ID NO: 1;

(b) a reverse primer that anneals to a *Cryptococcus neoformans* consensus sequence consisting essentially of nucleotides 1512-1533 of SEQ ID NO: 2;

(c) a hybridization probe having a nucleotide sequence consisting essentially of a sequence set forth in SEQ ID NO: 5, wherein the probe has a fluorescent moiety; and (d) instructions for using the forward primer, reverse primer and hybridization probe in performing real-time PCR in detecting the presence of *Cryptococcus neoformans*.

In other example embodiments, kits are provided for real-time PCR for detection of *Cryptococcus neoformans*, which include:
(a) a forward primer that anneals to a *Cryptococcus neoformans* consensus sequence consisting essentially of nucleotides 1480-1499 of SEQ ID NO: 1;
(b) a reverse primer that anneals to a *Cryptococcus neoformans* consensus sequence consisting essentially of nucleotides 1165-1184 of SEQ ID NO: 2;
(c) a hybridization probe having a nucleotide sequence consisting essentially of a sequence set forth in SEQ ID NO: 5, wherein the oligonucleotide probe has a fluorescent moiety; and
(d) instructions for using the forward primer, reverse primer and hybridization probe in performing real-time PCR in detecting the presence of *Cryptococcus neoformans*.

In other example embodiments, kits are provided for real-time PCR for detection of *Cryptococcus neoformans*, which include:
(a) a forward primer that anneals to a *Cryptococcus neoformans* consensus sequence consisting essentially of nucleotides 2105-2124 of SEQ ID NO: 1;
(b) a reverse primer that anneals to a *Cryptococcus neoformans* consensus sequence consisting essentially of nucleotides 508-527 of SEQ ID NO: 2;
(c) a hybridization probe having a nucleotide sequence consisting essentially of a sequence set forth in SEQ ID NO: 5, wherein the oligonucleotide probe has a fluorescent moiety; and
(d) instructions for using the forward primer, reverse primer and hybridization probe in performing real-time PCR in detecting the presence of *Cryptococcus neoformans*.

BRIEF DESCRIPTION OF THE FIGURES

Embodiments of the invention are herein described, by way of non-limiting example, with reference to the following accompanying Figures:

FIG. 1 depicts the nucleotide sequence of the fungal specific transcription factor gene (the plus strand) from *Cryptococcus neoformans* (SEQ ID NO: 1). The sequence complementary to the primers (i.e., Cneo F1 and Cneo R1) and hybridization probe (i.e., Cneo Probe) used in PCR is bold-faced. The nucleotide sequence of fungal specific transcription factor gene is available from GenBank Accession Number AE017349.

DETAILED DESCRIPTION

Figure 2:
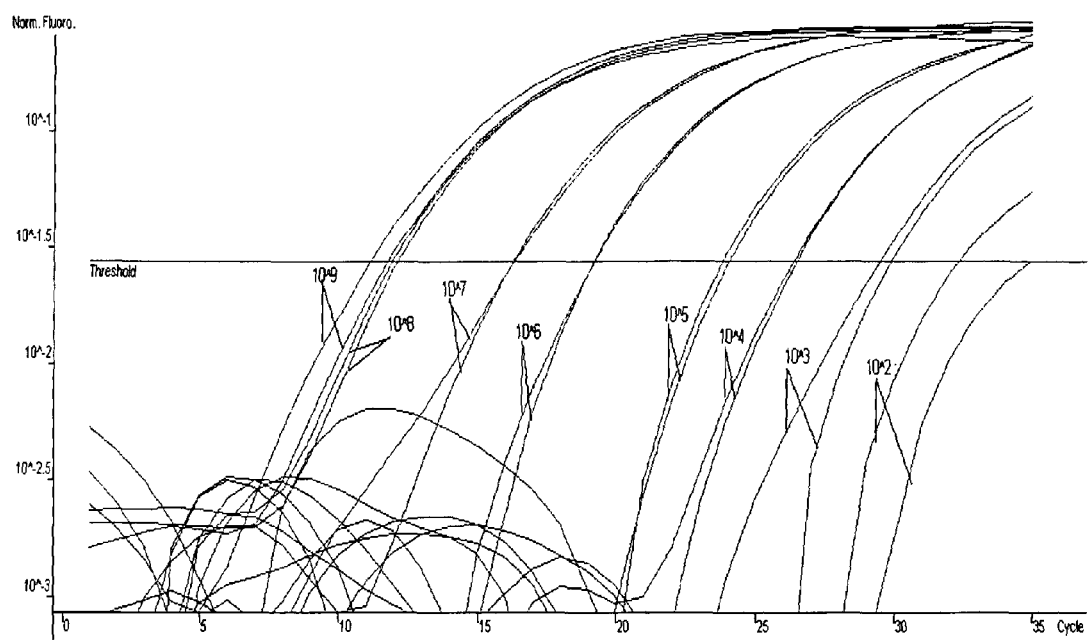
FIG. 2 depicts the linear range of detection of the *Cryptococcus neoformans* fungal specific transcription factor gene by Real-Time PCR. The pCneoJE plasmid dilutions (in duplicate) are $1 \times 10^9$, $1 \times 10^8$, $1 \times 10^7$, $1 \times 10^6$, $1 \times 10^5$, $1 \times 10^4$, $1 \times 10^3$, and $1 \times 10^2$ copies/reaction. Using 35 cycles, the real-time PCR assay is reproducibly detecting as well as 100 copies/reaction.

The aspects, advantages and/or other features of example embodiments of the invention will become apparent in view of the following detailed description, taken in conjunction with the accompanying drawings. It should be apparent to those skilled in the art that the described embodiments of the present invention provided herein are merely exemplary and illustrative and not limiting. Numerous embodiments of modifications thereof are contemplated as falling within the scope of the present invention and equivalents thereto. All publications, patent applications, patents, and other references mentioned herein are incorporated by reference in their entirety.

Provided herein are sensitive and specific methods using PCR, such as real-time PCR, to detect the presence of *Cryptococcus neoformans* in a biological sample. In accordance with example embodiments primers and probes are also provided, which may be used to detect *Cryptococcus neoformans*. Also provided are kits including such primers and/or probes. Embodiments of the present invention provide much-needed increased sensitivity of real-time PCR and are proven to have high specificity.

In describing example embodiments, specific terminology is employed for the sake of clarity. However, the embodiments are not intended to be limited to this specific terminology. As used herein, the term "primer" refers to a nucleotide sequence which can be extended by template-directed polymerization. For the purpose of this application, the term "nucleotide sequence" is intended to include DNA or modification thereof.

As used herein, the term "isolated" refers to a nucleic acid separated from its natural source.

As used herein, an "isolated" oligonucleotide refers to an oligonucleotide that is synthesized chemically (not a naturally occurring nucleic acid).

As used herein, "a" or "an" may mean one or more. As used herein, "another" may mean at least a second or more.

As indicated above, the term "consisting essentially of," throughout this application is intended to encompass sequences having at least 99%, 95% or 90% identity to those identified herein.

As used herein, the term "biological sample" may include but are not limited to urine, fluid or tissue samples such as blood (e.g., whole blood, blood serum, etc), bronchoalveolar lavage, nasal swabs, cerebrospinal fluid, synovial fluid, brain and other neurological tissues, cardiac tissue, skin, lymph nodes, and the like from a mammal such as a human or domestic animal. Extraction of nucleic acids from biological samples is known to those of skill in the art.

Oligonucleotide Primers of the Invention

A. Oligonucleotide Primer Sets Target Against the Fungal Specific Transcription Factor Gene of *Cryptococcus neoformans*

The present inventors discovered, inter alia, a PCR assay to detect specifically *Cryptococcus neoformans* by amplifying, for example, a portion of the fungal specific transcription factor gene located in chromosome 9 of *Cryptococcus neoformans* var. *neoformans* strain JEC21. The fungal specific transcription factor gene encodes a transcriptional protein in *Cryptococcus neoformans*. The full length nucleotide sequence of the fungal specific transcription factor gene in *Cryptococcus neoformans* var. *neoformanis* strain JEC21 is publicly available. (National Center for biotechnology Information Access No. 57228846, the entire content of which is hereby incorporated by reference). The fungal specific transcription factor gene contains two polynucleotide strands (i.e., a 5' to 3' "plus" strand and a 3' to 5' "minus" strand). The nucleotide sequence of SEQ ID NO: 1 represents the plus strand (See, FIG. 1). The nucleotide sequence of SEQ ID NO: 2 represents the minus (i.e., reverse complementary) strand of the nucleotide sequence of SEQ ID NO: 1.

In *Cryptococcus neoformans*, ribosomal RNA (rRNA) has been used in PCR detection. (See, e.g., U.S. Pat. Nos. 5,464,743, 5,580,971, 5,763,163, 5,763,169, 5,707,802, and 6,180,339). However, the PCR amplification of the rRNA is not specific (i.e., the primers used to detect rRNA in *Cryptococcus neoformans* also detect other microorganisms). Contrary to the methods using the rRNA, the present inventors discovered that the fungal specific transcription factor gene is highly specific for the detection of *Cryptococcus neoformans*.

Example embodiments herein are therefore drawn to isolated oligonucleotide primers and primer sets, which are capable of annealing under highly stringent hybridization conditions, including PCR conditions, and real-time PCR conditions, to a segment of the fungal transcription factor gene of *Cryptococcus neoformans*. As used herein, a primer set contains a pair of primers; that is, a forward primer and a reverse primer. In an example embodiment, the primer set (i.e., forward primer and reverse primer) sufficiently anneals to the fungal specific transcription factor gene segment during the PCR conditions; such as real-time PCR conditions.

Highly stringent hybridization conditions include the following conditions: 6×SSC and 65° C.; highly stringent hybridization conditions described in Ausubel et al., 2002, Short Protocols in Molecular Biology, 5$^{th}$ edition, Volumes 1 and 2, John Wiley & Sons, Inc., Hoboken, N.J., the entire contents of which are hereby incorporated by reference; and highly stringent hybridization conditions described in Ausubel et al., 1997, Short Protocols in Molecular Biology, 3$^{rd}$ edition, John Wiley & Sons, Inc., New York, N.Y., the entire contents of which are hereby incorporated by reference.

Example embodiments also relate to labeled nucleic acids that can act as probes (i.e., hybridization probes) to facilitate the detection of an amplification product of *Cryptococcus neoformans*, using an isolated oligonucleotide primer set. According to example embodiments, when hybridized to the target gene (e.g., fungal specific transcription factor gene), the hybridization probe (which may carry a fluorescent moiety such as a fluorescein moiety on its 5' end and a quencher on its 3' end or a fluorescent moiety on its 3' end and a quencher on its 5' end), is degraded when there is successful amplification initiated by the forward primer and reverse primer against the target gene.

The design of specific primers and hybridization probes may be performed, for example, using a computer program such as Beacon Designer 4.02 (Build 402003) (PREMIER Biosoft International, Palo Alto, Calif.). Other equivalent computer programs such as OLIGO (Molecular Biology Insights, Inc., Cascade, Colo.) may also be used. One of ordinary skill in the art would appreciate the various factors in the primer design. The factors may include, but are not limited to, melting temperatures of the primer pairs, length of the primers or probes and size of the amplicon products. Embodiments of the present invention are not limited to the specific primers and hybridization probes explicitly provided herein. For example, other primers that amplify the fungal specific transcription factor gene of *Cryptococcus neoformans* may be used in accordance with the present invention.

As used herein, the term "Cneo primers" refers to oligonucleotide primers (i.e., a forward primer—Cneo F and a reverse primer—Cneo R) that anneal specifically to the fungal specific transcription factor gene in *Cryptococcus neoformans* and thus initiate the amplifying process under PCR conditions. A first primer set contains a forward primer ("Cneo F1") and a reverse primer ("Cneo R1"). A second primer set contains a forward primer ("Cneo F2") and a reverse primer ("Cneo R2"). A third primer set contains a forward primer ("Cneo F3") and a reverse primer ("Cneo R3"). As used herein, the term "amplifying" refers to a process of synthesizing nucleic acid molecules that are complementary to both strands of a template nucleic acid molecule (e.g., fungal specific transcription factor gene). Amplifying during a PCR reaction typically involves several steps such as denaturing the template nucleic acid (at an elevated temperature), annealing primers to the template nucleic acid (at a temperature which is below the melting temperature of the primers), and elongating from the primers to produce an amplicon. It is to be understood that amplification typically requires the substrates (i.e., deoxyribonucleoside triphosphates) and a DNA polymerase enzyme (e.g., Taq DNA polymerase) as well as appropriate buffer and co-factors (e.g., magnesium chloride etc). The optimal concentrations of amplification substrates, enzyme and co-factors can conveniently be determined by one skilled in the art.

B. Forward Primers of the Fungal Specific Transcription Factor of *Cryptococcus neoformans*

In example embodiments, a plurality of forward primers is provided. Typically, oligonucleotide forward primers are 15-25 nucleotides in length. Primers useful in such embodiments may include e.g., an oligonucleotide primer capable of annealing within a portion of the fungal specific transcription factor gene in *Cryptococcus neoformans*, and thus providing a point of initiation in nucleic acid synthesis in a PCR process. A forward primer typically is single-stranded, and is designed to anneal to either the plus strand or minus strand of the fungal specific transcription factor gene.

In a first example embodiment, the nucleotide sequence of a forward primer (i.e., Cneo F1; sequence consisting essentially of the sequence set forth in SEQ ID NO: 3) corresponds to the fungal specific transcription factor gene segment of the plus strand which consists essentially of the nucleotides 1121 through 1144 of SEQ ID NO: 1 (See, FIG. 1). This particular forward primer is capable of annealing to the minus strand spanning the bases 1617 through 1640.

In a second example embodiment, the nucleotide sequence of another forward primer (i.e., Cneo F2; sequence consisting essentially of the sequence set forth in SEQ ID NO: 6) corresponds to the fungal specific transcription factor gene segment of the plus strand which consists essentially of the nucleotides 1480 through 1499 of SEQ ID NO: 1. This particular forward primer is capable of annealing to the minus strand spanning the bases 1262 through 1281.

In a third example embodiment, the nucleotide sequence of another forward primer (i.e., Cneo F3; sequence consisting essentially of the sequence set forth in SEQ ID NO: 8) corresponds to the fungal specific transcription factor gene segment of the plus strand which consists essentially of the nucleotides 2105 through 2124 of SEQ ID NO: 1. This particular forward primer is capable of annealing to the minus strand spanning the bases through 637 through 656.

Accordingly, the forward primers consist of the nucleotide sequence of SEQ ID NO: 3, SEQ ID NO: 6, or SEQ ID NO: 8 (as well as sequences having at least about 99%, 95%, or 90% identity thereto, as described further below).

C. Reverse Primers of the Fungal Specific Transcription Factor Gene of *Cryptococcus neoformans*

In example embodiments, a plurality of reverse primers is provided. As with the forward primers, oligonucleotide reverse primers may be 15-25 nucleotides in length. Reverse primers useful in the present invention may include oligonucleotide reverse primers, in conjunction with the forward primers, which anneal to a different portion and on a different strand of the fungal specific transcription factor gene in *Cryptococcus neoformans*, thus providing an appropriate amplicon product in PCR. Similar to the forward primers, the reverse primers may be single-stranded and can anneal to either the plus strand or minus strand of the fungal specific transcription factor gene. When forward primer anneals to the plus strand, reverse primer anneals to the minus strand, and vice versa.

In a first example embodiment, the nucleotide sequence of a reverse primer (i.e., Cneo R1; sequence consisting essentially of the sequence set forth in SEQ ID NO: 4) corresponds to the fungal specific transcription factor gene segment of the minus strand which consists essentially of the nucleotides 1512 through 1533 of SEQ ID NO: 2 (See, FIG. 1). This particular reverse primer is capable of annealing to the plus strand spanning the bases 1228-1249.

In a second example embodiment, the nucleotide sequence of a reverse primer (i.e., Cneo R2; sequence consisting essentially of the sequence set forth in SEQ ID NO: 7) corresponds to the fungal specific transcription factor gene segment of the minus strand which consists essentially of the nucleotides 1165 through 1184 of SEQ ID NO: 2. This particular reverse primer is capable of annealing to the plus strand spanning the bases 1577-1596.

In a third example embodiment, the nucleotide sequence of a reverse primer (i.e., Cneo R3; sequence consisting essentially of the sequence set forth in SEQ ID NO: 9) corresponds to the fungal specific transcription factor gene segment of the minus strand which consists essentially of the nucleotides 508 through 527 of SEQ ID NO: 2. This particular reverse primer is capable of annealing to the plus strand spanning the bases 2234-2253.

Thus, according to example embodiments, the reverse primers consist of the nucleotide sequence of SEQ ID NO: 4, SEQ ID NO: 7, or SEQ ID NO: 9 (as well as sequences having at least about 99%, 95%, or 90% identity thereto, as described further below).

Given what is disclosed herein, one of ordinary skill in the art would know how to design and prepare primer sets that are useful in amplifying a segment of the fungal specific transcription factor gene in *Cryptococcus neoformans*. As indicated above, the primers and primer sets provided are merely exemplary.

D. Example Primer Sets

The primer sets are used in combination with PCR reagents under reaction conditions to initiate primer extension. A primer set useful in the present embodiments, may include a forward primer that anneals to one strand of the fungal specific transcription factor gene, and a reverse primer that anneals to the opposing strand of the fungal specific transcription factor gene. The location between the forward primers and reverse primers may be optimized with a computer program to yield an appropriate amplicon size.

In example embodiments, a first primer set is provided, which includes a forward primer (Cneo F1) having the nucleotide sequence as set forth in SEQ ID NO: 3 and a reverse primer (Cneo R1) having the nucleotide sequence as set forth in SEQ ID NO: 4.

In other example embodiments, a second primer set is provided, which includes a forward primer (Cneo F2) having the nucleotide sequence as set forth in SEQ ID NO: 6, and a reverse primer (Cneo R2) having the nucleotide sequence as set forth in SEQ ID NO: 7.

In other example embodiments, a third primer set is provided, which includes a forward primer (Cneo F3) having the nucleotide sequence as set forth in SEQ ID NO: 8, and a reverse primer (Cneo R3) having the nucleotide sequence as set forth in SEQ ID NO: 9.

E. Polynucleotide Length of Primers

One of ordinary skill in the art would recognize the nucleotide length required for the primer set and would be able to conveniently determine the optimal length of the primers. In example embodiments, the primers have about 15-25 basepairs (bp) in length. According to further example embodiments, the primers have about 20-22 bp nucleotides.

F. Primers with High Percent Sequence Identity to Sufficiently Anneal During PCR It is understood that the nucleotide sequence of the primers that anneal to the fungal specific transcription factor gene in *Cryptococcus neoformans* may somewhat vary without affecting its annealing ability in a PCR reaction. Thus, the present methods, primers, and kits are intended to encompass these slight variations.

In example embodiments, the forward primer is at least about 99% identical to the fungal transcription factor gene segment corresponding to the nucleotide sequence set forth in SEQ ID NO: 3, SEQ ID NO: 6, or SEQ ID NO: 8. According to further examples, the forward primer has at least about 95% identity to SEQ ID NO: 3, SEQ ID NO: 6 or SEQ ID NO: 8. According to even further examples, the forward primer has at least about 90% identity to SEQ ID NO: 3, SEQ ID NO: 6, or SEQ ID NO: 8.

In other example embodiments, the reverse primer is at least about 99% identical to the fungal specific transcription factor gene segment corresponding to the nucleotide sequence set forth in SEQ ID NO: 4, or SEQ ID NO: 7, or SEQ ID NO: 9. According to further examples, the reverse primer has at least about 95% identity to SEQ ID NO: 4, or SEQ ID NO: 7, or SEQ ID NO: 9. According to even further examples, the reverse primer has at least about 90% identity to SEQ ID NO: 4, or SEQ ID NO: 7, or SEQ ID NO: 9.

Example embodiments further include isolated oligonucleotide primers, wherein the oligonucleotide primers have at least 99%, 95%, or 90% identity to a nucleotide sequence selected from the group consisting of (a) nucleotides 1121-1144 of SEQ ID NO: 1, (b) nucleotides 1480-1499 of SEQ ID NO: 1, (c) nucleotides 2105-2124 of SEQ ID NO: 1, (d) nucleotides 1512-1533 of SEQ ID NO: 2, (e) nucleotides 1165-1184 of SEQ ID NO: 2, and (f) nucleotides 508-527 of SEQ ID NO: 2.

Pairwise nucleotide sequence alignments and determination of percent identities may be performed using the default parameters of the Clustal V algorithm or the Clustal W algorithm, wherein both algorithms are incorporated into the Power Macintosh MegAlign 6.1 program (DNASTAR, Madison, Wis.). The default parameters for pairwise alignments using the Clustal V algorithm are as follows: Ktuple=1, gap penalty=3, window=5, and diagonals=5. The default parameters for pairwise alignments using the Clustal W algorithm are as follows: gap penalty=10.00 and gap length=0.10. The Clustal V algorithm is described in Higgins et al., 1989, Fast and sensitive multiple sequence alignments on a microcomputer. Computer Applications in the Biosciences 5:151-153, the entire contents of which are hereby incorporated by reference. The Clustal W algorithm is described in Thompson et al., 1994, CLUSTAL W: improving the sensitivity of progressive multiple sequence alignment through sequence weighting, position specific gap penalties and weight matrix choice. Nucleic Acids Research 22:4673-80, the entire contents of which are hereby incorporated by reference. In other embodiments, the oligonucleotide and the segment of the polynucleotide include the same number of nucleotides.

Hybridization Probe of the Fungal Specific Transcription Factor Gene of *Cryptococcus neoformans*

Example embodiments are also drawn to isolated oligonucleotide hybridization probes capable of hybridizing under highly stringent hybridization conditions to a segment of a polynucleotide directed to the fungal specific transcription factor gene of *Cryptococcus neoformans*. In example embodiments, the hybridization probe may include a dual labeled hybridization probe or a molecular beacon.

As described further herein, example embodiments of PCR assays for detection of *Cryptococcus neoformans* include conventional PCR assays and real-time PCR assays. Real-time PCR offers a much-increased sensitivity for detection, as compared to conventional PCR, making it an ideal assay. A PCR assay in conjunction with fluorescence resonance energy transfer (FRET) technique may be employed for real-time PCR. In such an assay, a donor fluorescent moiety and a corresponding acceptor fluorescent moiety are positioned in such a manner that the energy transfer taking place between two fluorescent moieties can be detected and monitored via a machine. It is understood that the emission spectrum of an acceptor fluorescent moiety overlaps with the excitation spectrum of a donor fluorescent moiety. One of ordinary skill in the art would know how to select a fluorescent donor moiety and its corresponding acceptor moiety in FRET.

According to non-limiting example embodiments, TAQMAN® technology may be used to detect the presence of an amplification product, i.e., to detect the presence or absence of *Cryptococcus neoformans* in a real-time PCR assay. Typically, in FRET involving TAQMAN® technology to detect the presence of an amplification product, a hybridization probe is labeled with two fluorescent moieties. When a first fluorescent moiety is excited (e.g., light with specific wavelength), the absorbed energy is transferred to a second fluorescent moiety in accordance with the principle of FRET. When the second fluorescent moiety is a quencher molecule, the energy transferred is absorbed (i.e., quenched) and no detection of fluorescence emission can be detected. During the annealing step of a PCR reaction, a hybridization probe (dually labeled with two fluorescent moieties) is annealed to the fungal specific transcription factor gene. If a successful amplification reaction occurs, the Taq polymerase then degrades (attributed by the 5' to 3' exonuclease activity) the hybridization probe. The degradation of hybridization probe by Taq polymerase allows the first fluorescent moiety to be spatially separated from the second fluorescent moiety; thus permitting the detection of fluorescence emission (as the quencher fails to absorb the transferred energy).

Typically, hybridization probes are about 20-35 base pairs in length, so as to sufficiently anneal to the target nucleic acid molecules (i.e., fungal specific transcription factor gene). The primers may contain e.g., 30 nucleotides. As used herein, "Cneo Probe" refers to oligonucleotide probe that anneals specifically to the fungal specific transcription factor nucleic acid sequences and provide fluorescence signals during annealing of PCR polymerization.

In accordance with example embodiments, molecular beacon technology in conjunction with PCR may also be used. In this technology, a hybridization probe is also labeled with a first fluorescent moiety and a second fluorescent moiety. Like TAQMAN® technology, the second fluorescent moiety is generally a quencher. Typically, molecular beacon technology uses an oligonucleotide as a hybridization probe that permit hairpin formation (i.e., the hybridization probe contains nucleotide sequences to form a hairpin). As a result, the two fluorescent moieties present on the hybridization probe are in close proximity when in solution (due to hairpin formation). However, if there is a successful amplification and annealing, the hybridization probe anneals to the target nucleic acids and thus destroys the hairpin formation, separating the two florescent moieties and allowing the detection of the emission of fluorescent energy.

According to non-limiting example embodiments, an isolated hybridization probe is provided having a nucleotide sequence consisting essentially of a sequence complementary to consensus nucleotide sequence of nucleotides 1150-1178 of SEQ ID NO: 1 or 1583 through 1611 of SEQ ID NO: 2, where the hybridization probe includes at least one fluorescent moiety. According to example embodiments, the hybridization probe anneals to the fungal specific transcription factor gene segment consisting essentially of nucleotides 1150 through 1178 of SEQ ID NO: 1 (FIG. 1). In other example embodiments, the hybridization probe anneals to the fungal specific transcription factor gene segment consisting essentially of nucleotides 1583 through 1611 of SEQ ID NO: 2.

According to example embodiments, the hybridization probe includes at least one fluorescent moiety (or molecule), such as a fluorescein moiety. The fluorescent moiety may be located e.g., at the 5' end of the hybridization probe. Examples of suitable fluorescent moieties that may be used in accordance with real-time PCR methods would be known to those skilled in the art. For example fluorescent reporter or fluorophore (e.g. 6-carboxy-fluorescein, acronym: FAM, or tetrachlorofluorescein, acronym: TET) may be covalently attached to the 5' end of the probe. According to non-limiting example embodiments, the fluorescent molecule is a 6-carboxy-fluorescein moiety attached to the 5' end of the hybridization probe.

In further example embodiments, the hybridization probe may include a quencher. The fluorescent molecule emits its emission light and is quenched by a quencher during a real-time PCR reaction. The quencher may be attached to the opposite end of the hybridization probe from the fluorescent moiety, e.g., to the 3' end of the hybridization probe. Example quenchers may include e.g., BLACK HOLE QUENCHER® 1 (version 1 quencher of common fluorophores that emit light in the range of 430-730 nm), BLACK HOLE QUENCHER® 2 (version 2 quencher of common fluorophores that emit light in the range of 430-730 nm), IOWA BLACK® FQ (quencher of common fluorophores that emit light in the range of 420-620 nm), IOWA BLACK® RQ-sp (quencher of common fluorophores that emit light in the range of 500-700 nm), and the like.

In example embodiments, the hybridization probe consists essentially of nucleotide sequence of SEQ ID NO: 5, as well as at least one fluorescent moiety, and may further include a quencher.

It is understood that the nucleotide sequence of the isolated hybridization probe may also somewhat vary. The present methods, probes, and kits are intended to encompass these variations as well. In particular, according to example embodiments, hybridization probes may have at least 99%, 95% or 90% identity to a nucleotide sequence consisting essentially of SEQ ID NO: 5. Example embodiments also provide an isolated hybridization probe, which has at least about 99%, 95% or 90% identity to a nucleotide sequence complementary to consensus nucleotide sequence of nucleotides 1150 through 1178 of SEQ ID NO: 1 or nucleotides 1583 through 1611 of SEQ ID NO: 2.

Oligonucleotide Combinations of the Invention

Other embodiments are directed to a composition (e.g., a reaction mixture or a kit) including a first isolated oligonucleotide (e.g., a forward primer) and a second isolated oligonucleotide (e.g., a reverse primer).

In example embodiments, the composition includes a first forward primer which corresponds to (e.g., includes or consists essentially of) the nucleotides 1121 through 1144 of SEQ ID NO: 1 (i.e., SEQ ID NO: 3), and a first reverse primer which corresponds to (e.g., includes or consists essentially of) the nucleotides 1512 through 1533 of SEQ ID NO: 2 (i.e., SEQ ID NO: 4). The forward primer of SEQ ID NO: 3 and reverse primer of SEQ ID NO: 4 are capable of annealing under PCR conditions to the fungal specific transcription factor gene segment and produce an amplicon.

In other embodiments, the composition includes a second forward primer which corresponds to the nucleotides 1480 through 1499 of SEQ ID NO: 1. (i.e., SEQ ID NO: 6) and a second reverse primer which corresponds to the nucleotides 1165 through 1184 of SEQ ID NO: 2 (i.e., SEQ ID NO: 7). The forward primer of SEQ ID NO: 6 and reverse primer of SEQ ID NO: 7 are capable of annealing under PCR conditions to the fungal specific transcription factor gene segment and produce an amplicon.

In other embodiments, the composition includes a third forward primer which corresponds to the nucleotides 2105 through 2124 of SEQ ID NO: 1. (i.e., SEQ ID NO: 8) and a third reverse primer which corresponds to the nucleotides 508 through 527 of SEQ ID NO: 2 (i.e., SEQ ID NO: 9). The forward primer of SEQ ID NO: 8 and reverse primer of SEQ ID NO: 9 are capable of annealing under PCR conditions to the fungal specific transcription factor gene segment and produce an amplicon.

Example embodiments provide a sensitive and specific PCR assay to detect *Cryptococcus neoformans*. In example embodiments, hybridization probes are provided. The hybridization probe is capable of annealing to nucleotide sequences contained in SEQ ID NO: 1 or SEQ ID NO: 2. The hybridization probe may be about 20-35 nucleotides long. According to example embodiments, the hybridization probe is about 30 nucleotides long.

In example embodiments, the hybridization probe comprises the nucleotide sequence of SEQ ID NO: 5.

Methods

The present inventors discovered that the fungal specific transcription factor gene can be used as a diagnostic tool for determining the presence of *Cryptococcus neoformans* in biological samples obtained from mammals such as a human subject. Example embodiments pertains to methods for determining whether a sample (e.g., a biological sample such as urine) contains *Cryptococcus neoformans*, wherein the methods include the following: (a) mixing DNA extracted from a biological sample with a primer pair that targets fungal specific transcription factor gene of *Cryptococcus neoformans* (e.g., where the primer pair may be included in a composition) (b) amplifying, by a polymerase chain reaction, a segment of the nucleic acid (directed to the fungal specific transcription factor gene in *Cryptococcus neoformans*) to produce an amplicon, wherein production of the amplicon is primed by the forward and reverse primers, and (c) detecting a presence or absence of *Cryptococcus neoformans* in the sample if the amplicon is detected. The forward primer may be capable of annealing under PCR conditions to a polynucleotide consisting of the nucleotide sequence of SEQ ID NO: 2, wherein the reverse primer is capable of annealing to a polynucleotide consisting of the nucleotide sequence of SEQ ID NO: 1. As part of the present methods, a vessel containing the primer pair and biological vessel may be may be incubated under conditions allowing production of the amplicon if the sample contains *Cryptococcus neoformans*.

In other example embodiments, the forward primer may be capable of hybridizing under PCR conditions to a segment of a polynucleotide, wherein the segment consists essentially of nucleotides 1617 through 1640 of SEQ ID NO: 2. In another embodiment, the reverse primer may be capable of hybridizing under the same conditions to a segment of a polynucleotide, wherein the segment consists essentially of nucleotides 1228 through 1249 of SEQ ID NO: 1.

In another embodiment, the forward primer is at least 90%, 91%, 92%, 93%, 94%, 95%, 96%, 97%, 98%, or 99% identical to, or is 100% identical to a segment of a polynucleotide based on the Clustal V or W alignment method using the default parameters, wherein the first polynucleotide consists of the nucleotide sequence of SEQ ID NO: 1. In another embodiment, the forward primer and the segment of the polynucleotide contain the same number of nucleotides. In another embodiment, the reverse primer is at least 90%, 91%, 92%, 93%, 94%, 95%, 96%, 97%, 98%, or 99% identical to, or is 100% identical to a segment of a polynucleotide based on the Clustal V or W alignment method using the default parameters, wherein the second polynucleotide consists of the nucleotide sequence of SEQ ID NO: 2. In another embodiment, the reverse primer and the segment of the second polynucleotide contain the same number of nucleotides.

In another embodiment, the forward primer is at least 90%, 91%, 92%, 93%, 94%, 95%, 96%, 97%, 98%, or 99% identical to, or is 100% identical to a segment of a polynucleotide, wherein the segment consists of the reverse complement of nucleotides 508 through 527 of SEQ ID NO:2 based on the Clustal V or W alignment method using the default parameters. In another embodiment, the reverse primer is at least 90%, 91%, 92%, 93%, 94%, 95%, 96%, 97%, 98%, or 99% identical to, or is 100% identical to a segment of a polynucleotide, wherein the segment consists of the reverse complement of nucleotides 2234 through 2253 of SEQ ID NO: 1 based on the Clustal V or W alignment method using the default parameters.

In another embodiment, the forward primer consists of a nucleotide sequence comprised by the nucleotide sequence of SEQ ID NO: 1. In another embodiment the reverse primer consists of a nucleotide sequence comprised by the nucleotide sequence of SEQ ID NO:2. In another embodiment, the forward or forward primers comprise 15, 16, 17, 18, 19, 20, 21, 22, 23, 24, or 25 nucleotides. In another embodiment, the forward or reverse primers are 20-25 nucleotides long. In another embodiment, the forward primer includes a sequence consisting essentially of the nucleotide sequence of SEQ ID NO: 3, SEQ ID NO: 6, or SEQ ID NO: 8. In another embodiment, the reverse primer includes a sequence consisting essentially of the nucleotide sequence of SEQ ID NO: 4, SEQ ID NO: 7 or SEQ ID NO: 9.

Optionally, the mixing may include mixing a hybridization probe (e.g., a hybridization probe labeled with two fluorescent moieties in accordance with TAQMAN® technology or a molecular beacon) capable of detecting the amplicon if the amplicon is produced. In other embodiments, the oligonucleotide probe is capable of hybridizing under PCR conditions to a polynucleotide consisting of the nucleotide sequence of SEQ ID NO: 1 or SEQ ID NO: 2. In other embodiments, the oligonucleotide probe is capable of hybridizing under PCR conditions to a segment of a polynucleotide, wherein the segment consists essentially of nucleotides 1583 through 1611 of SEQ ID NO:2 or nucleotides 1150 through 1178 of SEQ ID NO:1.

In another embodiment, the hybridization probe is at least 90%, 91%, 92%, 93%, 94%, 95%, 96%, 97%, 98%, or 99% identical to, or is 100% identical to a segment of a polynucleotide based on the Clustal V or W alignment method using the default parameters, wherein the polynucleotide consists essentially of the nucleotide sequence of SEQ ID NO: 1 or SEQ ID NO: 2. In another embodiment, the oligonucleotide probe and the segment of the polynucleotide contain the same number of nucleotides.

In another embodiment, the oligonucleotide probe is at least 90%, 91%, 92%, 93%, 94%, 95%, 96%, 97%, 98%, or 99% identical to, or is 100% identical to a segment of a polynucleotide, wherein the segment consists essentially of the reverse complement of nucleotides 1583 through 1611 of SEQ ID NO: 2 or nucleotides 1150 through 1178 of SEQ ID NO: 1 based on the Clustal V or W alignment method using the default parameters.

In other example embodiments, the oligonucleotide probe includes a nucleotide sequence comprised by the nucleotide sequence of SEQ ID NO: 1 or SEQ ID NO: 2. In another embodiment, the hybridization probe comprises 20, 21, 22, 23, 24, 25, 26, 27, 28, 29, 30, 31, 32, 33, 34, or 35 nucleotides. In another embodiment, the oligonucleotide probe is 30 nucleotides long. In another embodiment, the oligonucleotide probe consists essentially of the nucleotide sequence of SEQ ID NO: 5.

In other example embodiments, a 6-carboxy-fluorescein moiety is attached to the 5' end of the oligonucleotide probe. In another embodiment, a BLACK HOLE QUENCHER® 1 (version 1 quencher of common fluorophores that emit light in the range of 430-730 nm) moiety is attached to the 3' end of the oligonucleotide probe. In other embodiments, the amplicon is detected by the oligonucleotide probe during real-time PCR. If convenient PCR is used, the formation amplicon is detected by gel electrophoresis after the PCR is completed.

Non-limiting example embodiments include methods of detecting presence of *Cryptococcus neoformans* in a biological sample, that include:
   (a) mixing
      (i) DNA extracted from the biological sample,
      (ii) a primer pair comprising a forward primer and a reverse primer that target a fungal specific transcription factor gene of *Cryptococcus neoformans*, and
      (iii) a hybridization probe, in a PCR vessel, wherein the hybridization probe comprises a fluorescent moiety;
   (b) amplifying, in a real-time PCR reaction, under conditions to allow production of an amplicon; and
   (c) detecting a presence or absence of *Cryptococcus neoformans*, by detecting a presence or absence of a fluorescent signal resulting from the formation of the amplicon, wherein the presence of a fluorescent signal is indicative of the presence of *Cryptococcus neoformans*.

The primers, probes, fluorescent moieties and other aspects of these and other embodiments may be as described herein throughout.

PCR Detection Assay

Example embodiments provide utilizing amplification approaches to quickly determine the presence of a particular gene. For purposes of this application, "amplifying" refers to a process of synthesizing nucleic acid molecules that are complementary to one or both strands of a template nucleic acid. With respect to *Cryptococcus neoformans*, the present inventors discovered amplifying the fungal specific transcription factor gene to be a highly sensitive and specific approach to determine the presence of such microorganism. One would appreciate the extraction protocol by which DNA of fungi can be extracted. For example, DNA may be extracted from biological samples using the acid guanidinium thiocyanate-phenol-chloroform method (Chomczymski and Sacchi, *Analytical Biochemistry*, vol. 162, pp. 156-159, 1987). Also, one of ordinary skill in the art would appreciate that amplifying a nucleic acid molecule typically includes (i) denaturing the template nucleic acid, (ii) annealing primers to the template nucleic acid at a temperature that is below the melting temperatures of the primers, and (iii) enzymatically elongating from the primers to generate an amplification product. Although the denaturing, annealing and elongating steps can be performed once, they are generally performed multiple times. As the amount of amplification product increases (oftentimes exponentially), it increases the sensitivity of the assay. Typically, amplification requires the presence of a Taq DNA polymerase, an appropriate buffer and appropriate salts such as magnesium chloride or potassium chloride.

In example embodiments a real-time PCR assay is provided. The real-time PCR assay is more sensitive than a conventional PCR assay, (but conventional PCR assays may be alternatively utilized herewith). Aided with the help of DNA probe, the real-time PCR provides a quantum leap as a result of real-time detection. In real-time PCR assay, a fluorometer and a thermal cycler for the detection of fluorescence during the cycling process is used. A computer that communicates with the real-time machine collects fluorescence data. This data is displaced in a graphical format through software developed for real-time analysis.

In addition to the forward primer and reverse primer (directed to the gene of interest—the fungal specific transcription factor gene), a single-stranded hybridization probe is also used. The hybridization probe may be a short oligonucleotide, usually 20-35 bp in length, and is labeled with a fluorescent reporting dye attached to its 5'-end as well as a quencher molecule attached to its 3'-end. When a first fluorescent moiety is excited with light of a suitable wavelength, the absorbed energy is transferred to a second fluorescent moiety (i.e., quencher molecule) according to the principles of FRET. Because the probe is only 20-35 bp long, the reporter dye and quencher are in close proximity to each other and little fluorescence is detected. During the annealing step of the PCR reaction, the labeled hybridization probe binds to the target DNA (i.e., the amplification product). At the same time, Taq DNA polymerase extends from each primer. Because of its 5' to 3' exonuclease activity, the DNA polymerase cleaves the downstream hybridization probe during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected. By way of example, a Rotor-Gene System is used and is suitable for performing the methods described herein for detecting fungal specific transcription factor gene in *Cryptococcus neoformans*. Further information on PCR amplification and detection using a Rotor-Gene can conveniently be found on Corbett's website.

In alternative embodiments, suitable hybridization probes such as intercalating dye (e.g., Sybr-Green I) or molecular beacon probes can be used. Intercalating dyes can bind to the minor grove of DNA and yield fluorescence upon binding to double-strand DNA. Molecular beacon probes are based on a hairpin structure design with a reporter fluorescent dye on one end and a quencher molecule on the other. The hairpin structure causes the molecular beacon probe to fold when not hybridized. This brings the reporter and quencher molecules in close proximity with no fluorescence emitted. When the molecular beacon probe hybridizes to the template DNA, the hairpin structure is broken and the reporter dye is no long quenched and the real-time instrument detects fluorescence.

The range of the primer concentration can optimally be determined. The optimization involves performing a dilution series of the primer with a fixed amount of DNA template. The primer concentration may be between about 50 nM to 300 nM. An optimal primer concentration for a given reaction with a DNA template should result in a low Ct-(threshold concentration) value with a high increase in fluorescence (5 to 50 times) while the reaction without DNA template should give a high Ct-value.

Real-time PCR methods include performing at least one cycling step that includes amplifying and hybridizing. An amplification step includes contacting the biological sample (suspected of containing DNA of *Cryptococcus neoformans*) with a pair of Cneo-primers to produce a Cneo amplification product if a fungal specific transcription factor nucleic acid molecule is present in the biological sample. The forward and reverse primers anneal to a target within or adjacent to a fungal specific transcription factor nucleic acid molecule such that at least a portion of the amplification product contains nucleic acid sequence corresponding to fungal specific transcription factor and, more importantly, such that the amplification product contains the nucleic acid sequences that are complementary to fungal specific transcription factor gene probes. A hybridizing step also includes contacting the biological sample with a hybridization probe. The hybridization probe is complementary to either the 5' strand or 3' strand of the fungal specific transcription factor gene. According to example embodiments, the hybridization probe anneals to the fungal specific transcription factor gene. When the Cneo primers begin to anneal, the Taq polymerase breaks the hybridization probe and release donor fluorescent moiety as well as a corresponding acceptor fluorescent moiety. The method further includes detecting the presence or absence of FRET between the donor fluorescent moiety of the hybridization probe and the corresponding acceptor fluorescent moiety of the hybridization probe. Multiple cycling steps can be performed, e.g., in a thermocycler. The above-described methods for detecting fungal specific transcription factor gene gene in a biological sample using primers and probes directed toward fungal specific transcription factor gene also can be performed using other fungal specific transcription factor gene-specific primers and probes.

Within each thermocycler run, control samples can be cycled as well. Positive control samples can also amplify, for example, a plasmid construct containing *Cryptococcus neoformans* Cneo nucleic acid molecules. Such a plasmid control can be amplified internally (e.g., within each biological sample) or in separate samples run side-by-side with the patients' samples. Each thermocycler run also should include a negative control that, for example, lacks *Cryptococcus neoformans* Cneo template DNA. Such controls are indicators of the success or failure of the amplification, hybridization, and/or FRET reaction. Therefore, control reactions can readily determine, for example, the ability of primers to anneal with sequence-specificity and to initiate elongation, as well as the ability of probes to hybridize with sequence-specificity and for FRET to occur.

Real-Time PCR Detection Kit for *Cryptococcus neoformans*

Example embodiments provide kits of manufacture, which may be used to detect specifically *Cryptococcus neoformans*. An article of manufacture (i.e., kit) according to the present invention includes a set of primers (i.e., a forward primer and a reverse primer) (directed to fungal specific transcription factor gene) and optionally a hybridization probe (directed to fungal specific transcription factor gene) used to detect *Cryptococcus neoformans*, contained within a suitable packaging material. Representative primers and hybridization probes provided in the kit for detection of *Cryptococcus neoformans* can be complementary to the fungal specific transcription factor gene encoding an outer surface membrane protein for *Cryptococcus neoformans*.

In embodiments including a hybridization probe, the hybridization probe may be conveniently labeled with a fluorescent moiety e.g., at its 5'-end and a quencher moiety at its 3'-end. Examples of suitable FRET donor fluorescent moieties and acceptor fluorescent moieties are provided herein. Alternatively, the hybridization probes supplied with the kit can be labeled. For example, an article of manufacture may include an instruction to tag the hybridization probe with a donor fluorescent moiety at its 5'-end and a corresponding acceptor fluorescent moiety at its 3'-end.

Methods of designing primers and hybridization probes are disclosed herein, and representative examples of primers and hybridization probes that amplify and hybridize to fungal specific transcription factor nucleic acids encoding a transcription protein are provided.

Articles of manufacture or kits provided herein may also include instructions, such as a package insert having instructions thereon, for using the primers to detect of the presence of *Cryptococcus neoformans* in a biological sample. Such instructions may be for using the primer pairs and/or the hybridization probes to specifically detect *Cryptococcus neoformans* in a biological sample.

Non-limiting example embodiments may include kits for PCR detection of *Cryptococcus neoformans*, which include the following:
  (a) a forward primer that anneals to a *Cryptococcus neoformans* consensus sequence consisting essentially of nucleotides 1121-1144 of SEQ ID NO: 1;
  (b) a reverse primer that anneals to a *Cryptococcus neoformans* consensus sequence consisting essentially of nucleotides 1512-1533 of SEQ ID NO: 2; and
  (c) instructions for using the forward primer and reverse primer in performing PCR to detect a presence of *Cryptococcus neoformans* in a sample.

Other non-limiting example embodiments may include kits for PCR detection of *Cryptococcus neoformans*, which include:
  (a) a forward primer that anneals to a *Cryptococcus neoformans* consensus sequence consisting essentially of nucleotides 1480-1499 of SEQ ID NO: 1;
  (b) a reverse primer that anneals to a *Cryptococcus neoformans* consensus sequence consisting essentially of nucleotides 1165-1184 of SEQ ID NO: 2; and (c) instructions for using the forward primer and reverse primer in performing PCR to detect a presence of *Cryptococcus neoformans* in a sample.

Other non-limiting example embodiments may include kits for PCR detection of *Cryptococcus neoformans*, which include:

(a) a forward primer that anneals to a *Cryptococcus neoformans* consensus sequence consisting essentially of nucleotides 2105-2124 of SEQ ID NO: 1;

(b) a reverse primer that anneals to a *Cryptococcus neoformans* consensus sequence consisting essentially of nucleotides 508-527 of SEQ ID NO: 2; and (c) instructions for using the forward primer and reverse primer in performing PCR to detect a presence of *Cryptococcus neoformans* in a sample.

According to non-limiting example embodiments, the kits may further include at least one hybridization probe having a nucleotide sequence consisting essentially of a sequence set forth in SEQ ID NO: 5, wherein the probe includes at least one fluorescent moiety; and the instructions may include instructions for using the forward primer, reverse primer and hybridization probe in performing real-time PCR in detecting a presence of *Cryptococcus neoformans* in a sample.

Articles of manufacture and kits provided herein may additionally include reagents for carrying out the methods disclosed herein (e.g., buffers, Taq polymerase enzymes, co-factors, and agents to prevent contamination). Such reagents may be specific for one of the commercially available instruments described herein.

The following examples are provided to further illustrate various non-limiting embodiments and techniques. It should be understood, however, that these examples are meant to be illustrative and do not limit the scope of the claims. As would be apparent to skilled artisans, many variations and modifications are intended to be encompassed within the spirit and scope of the invention.

EXPERIMENTAL EXAMPLES

Example 1

PCR Conditions for the Testing of Clinical Samples (a) Nucleotide Sequences for the Primers and Hybridization Probes Nucleotide sequences of primer sets and hybridization probes were determined from the nucleotide sequences of SEQ ID NO: 1 and SEQ ID NO: 2, using computer programs of Beacon Designer 4.02 (Build 402003) (PREMIER Biosoft International, Palo Alto, Calif.). Primer sets and hybridization probes having the specified nucleotide sequences were purchased from Integrated DNA Technologies (Stokie, Ill.). The primer set includes the first forward primer (Cneo F1), and the first reverse primer (Cneo R1) (See, details in FIG. 1).

(b) PCR Conditions

For the testing of clinical samples, each PCR was conducted in a volume of 25 μl containing the following: DNA extracted from a clinical sample (e.g., 500 ng), 600 nM of a forward primer, which has the nucleotide sequence set forth in SEQ ID NO:3 ("the Cneo F1"), 600 nM of a reverse primer, which has the nucleotide sequence set forth in SEQ ID NO: 4 ("the Cneo R1"), 200 nM of a hybridization probe, which has the nucleotide sequence set forth in SEQ ID NO: 5 ("the Cneo Probe"), and 1×MDL Custom qPCR SuperMix (Quanta BioSciences, Inc., Gaithersburg, Md.). The hybridization probe ("the Cneo Probe") has a 6-carboxy-fluorescein moiety and a Black Hole Quencher 1 moiety attached to its 5'-end and 3'-end, respective. 1×MDL Custom qPCR SuperMix has a Quanta BioSciences catalog number of 172-5008, and the 2× stock solution of the SuperMix contained 50 U/ml of AccuStart™ Taq DNA polymerase, 40 mM Tris-HCl (pH 8.4), 100 mM KCl, 6 mM $MgCl_2$, 400 nM dATP, 400 nM dCTP, 400 nM dGTP, 800 nM dUTP, 40 U/ml of UNG, and proprietary stabilizers of Quanta BioSciences, Inc. The Cneo probe was present in the reaction mixture to monitor real-time synthesis of the amplicon resulting from each successful PCR. The Cneo F1 primer, the Cneo R1 primer, and the Cneo Probe were used at 600 nM and 200 nM, respectively.

(c) Real-Time PCR

Real-Time PCR was conducted using the Rotor-Gene 3000 platform (Corbett Research, Sydney, Australia). Parameters for each PCR were as follows: an initial incubation at 50° C. for 2 minutes to activate UNG, followed by incubation at 94° C. for 3 minutes to initially denature the DNA, inactivate the UNG, and activate the AccuStart™ Taq DNA polymerase. Next, 35 cycles of denaturation (95° C. for 15 seconds), and an annealing and extension (65° C. for 60 seconds) were performed with fluorescence acquisition (excitation at 470 nM and emission at 510 nM) immediately following each annealing and extension step. Fluorescence curves were analyzed with dynamic-tube normalization, slope correction, and automatic threshold determination by a best-fit line of three concentrations of the positive-control standard DNA using Corbett Robotics Rotor Gene software version 6.0.31 (Corbett Research, Sydney, Australia). The three concentrations of the positive-control standard DNA were $1\times10^3$, $1\times10^5$ and $1\times10^7$ copies per reaction of pCneoJE (a plasmid which is described in Example 2). Negative template control (NTC) refers to plasmid lacking a template DNA and NTC threshold was set to a maximum 10%. The amplification target for *Cryptococcus neoformans* fungal specific transcription factor on chromosome 9, and successful amplification would result in a 129 bp amplicon product.

Example 2

Positive-Control Standard DNA for the PCR

A positive-control standard DNA for the PCR used was prepared from *Cryptococcus neoformans* (commercially available, ATCC® No. 22344). PCR amplification was conducted using 200 ng of DNA extracted *Cryptococcus neoformans*. Parameters for this PCR were as follows: an initial incubation at 94° C. for 3 minutes, followed by 40 cycles of incubation at 94° C. for 1 minute, 65° C. for 1 minute, and 72° C. for 2 minutes, followed by a final incubation at 72° C. for 10 minutes. All other conditions for this reaction were similar to those described in Example 1. The resulting amplicon was cloned into the pCR®2.1-TOPO® vector (Invitrogen, Carlsbad, Calif.) to produce pCneoJE, which was used as the positive-control standard DNA.

Different dilutions of pCneoJE plasmid were prepared and the range of dilution includes $1\times10^9$, $1\times10^8$, $1\times10^7$, $1\times10^6$, $1\times10^5$, $1\times10^4$, $1\times10^3$, and $1\times10^3$ copies/dilution. The pCneoJE dilutions were run in a real-time PCR. As shown in FIG. 2, real-time PCR detects fluorescence at a range of concentrations ranging from $1\times10^9$ to $1\times10^2$ copies/dilutions, indicating that the primer set and PCR conditions are optimal in detecting *Cryptococcus neoformans*. After 36 PCR cycles, the assay reproducibly detects as few as 100 copies/reaction. (See, FIG. 2). The data indicate this real-time PCR in the detection of *Cryptococcus neoformans* is highly sensitive.

Example 3

Specificity of the PCR Using Primers Directed to the Fungal Specific Transcription Factor Gene in *Cryptococcus neoformans*

Figure 3:
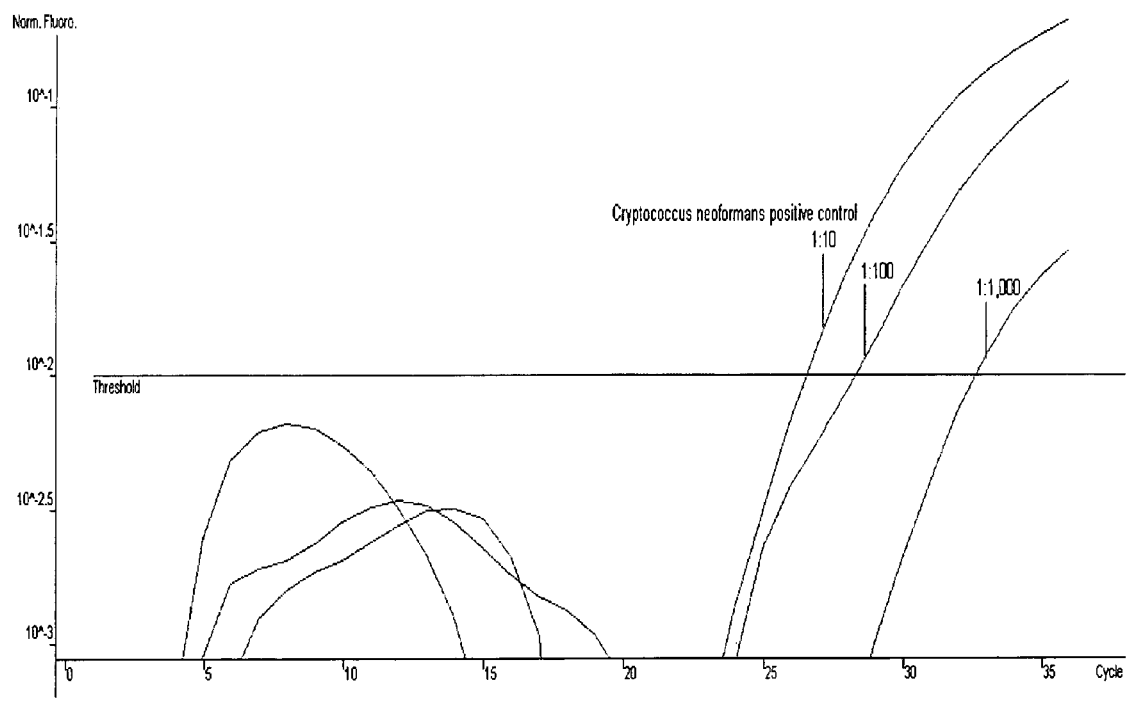
FIG. 3 depicts cross-reactivity analysis using real-time PCR with the primer (i.e., Cneo F1 and Cneo R1) in *Cryptococcus neoformans*. Quantitation data displays the serial dilutions of 1:10, 1:100 and 1:1,000 of the *Cryptococcus neoformans* ATCC positive control. No amplification is shown in the ten cocktails tested and the content of each pathogen cocktail is available in Table 1.

The specificity of the PCR utilizing the combination of the Cneo F primer, the Cneo R primer, and the Cneo probe was assessed by attempting to conduct real-time PCRs at varying dilutions of extracted DNA from *Cryptococcus neoformans* obtained from ATCC source (ATCC® No. 2344). As shown in FIG. 3, real-time PCR detects positive reactivity towards *Cryptococcus neoformans* at dilutions of 1:10, 1:100, 1:1,000.

We next tested forty-seven (47) species listed in the 10 cocktail formats. Duplicate reaction mixtures were tested and each reaction mixture contained DNA extracted from four or five types of pathogen summarized in Table 1. Each pathogen was purchased from ATCC®, except for *Candida lusitaneae* which was purchased from MicroBioLogics Inc. (Saint Cloud, Minn.).

TABLE 1

| | Number |
|---|---|
| Cocktail 1 | |
| *Gardnerella vaginalis* | ATCC ® No. 14018 |
| *Neisseria gonorrhoeae* | ATCC ® No. 27628 |
| *Trichomonas vaginalis* | ATCC ® No. 30246 |
| *Ureaplasma urealyticum* | ATCC ® No. 27618 |
| *Chlamydia trachomatis* | ATCC ® No. VR-901B |
| Cocktail 2 | |
| *Bacteroides fragilis* | ATCC ® No. 23745 |
| *Mobiluncus curtisii* | ATCC ® No. 35241 |
| *Mobiluncus mulieris* | ATCC ® No. 35243 |
| HTLV-I | ATCC ® No. CRL-8294 |
| Human herpesvirus 6B | ATCC ® No. VR-1467 |
| Cocktail 3 | |
| Herpes simplex virus 1 | ATCC ® No. VR-539 |
| Herpes simplex virus 2 | ATCC ® No. VR-734 |
| Human Papillomavirus | ATCC ® No. CRL-1550 |
| Epstein-Barr virus | ATCC ® No. CCL-86 |
| Cytomegalovirus | ATCC ® No. VR-807 |
| Cocktail 4 | |
| *Candida albicans* | ATCC ® No. 11651 |
| *Candida glabrata* | ATCC ® No. 2001 |
| *Candida parapsilosis* | ATCC ® No. 22019 |
| *Candida tropicalis* | ATCC ® No. 13803 |
| *Aspergillus fumigatus* | ATCC ® No. 14110 |
| Cocktail 5 | |
| *Mycoplasma fermentans* | ATCC ® No. 15474 |
| *Mycoplasma pneumoniae* | ATCC ® No. 15377 |
| *Mycoplasma genitalium* | ATCC ® No. 33530 |
| *Mycoplasma penetrans* | ATCC ® No. 55252 |
| *Mycoplasma hominis* | ATCC ® No. 14027 |
| Cocktail 6 | |
| Human herpesvirus-8 | ATCC ® No. CRL-2230 |
| Adenovirus type 1 | ATCC ® No. VR-1 |
| Coxsackievirus | ATCC ® No. VR-184 |
| *Babesia microti* | ATCC ® No. 30222 |
| Cocktail 7 | |
| *Chlamydia pneumoniae* | ATCC ® No. VR-1356 |
| *Helicobacter pylori* | ATCC ® No. 43579 |
| *Brucella ovis* | ATCC ® No. 25840 |
| *Borrelia burgdorferi* | ATCC ® No. 35210 |
| Canine herpesvirus | ATCC ® No. VR-552 |
| Cocktail 8 | |

TABLE 1-continued

| | Number |
|---|---|
| *Bartonella henselae* | ATCC ® No. 49882 |
| *Bartonella bacilliformis* | ATCC ® No. 35686 |
| *Bartonella Quintana* | ATCC ® No. 51694 |
| *Trichosporon cutaneum* | ATCC ® No. 4151 |
| Cocktail 9 | |
| Influenza virus A | ATCC ® No. VR-1520 |
| *Haemophilus parainfluenzae* | ATCC ® No. 7901 |
| Human rhinovirus 6 | ATCC ® No. VR-1116AS/GP |
| Human rhinovirus 11 | ATCC ® No. VR-1121 |
| Adenovirus type 10 | ATCC ® No. VR-11 |
| Cocktail 10 | |
| *Candida krusei* | ATCC ® No. 14243 |
| *Candida lusitaniae* | MicroBioLogics No. 0774P |
| *Candida dubliniensis* | ATCC ® No. MYA-179 |
| *Candida utilis* | ATCC ® No. 9226 |

FIG. 3 depicts an exemplary quantitation data display in real-time PCR. While we observed amplification with various dilutions of extracted DNA of *Cryptococcus neoformans*, no amplification is seen in the eight cocktails tested (i.e., cocktails 1-10) (i.e., fluorescence below Ct threshold; see FIG. 3). The contents of each pathogen cocktail are listed in Table 1.

Further shown in the following Table 2, no PCR amplification was observed in any of the cocktails tested (i.e., cocktails 1-10). In this series of studies, two samples were run separately. Neither of the two reaction mixtures containing DNA from Cocktails 1 through 10 was positive when using the combination of the Cneo F1 primer, Cneo R1 primer and the Cneo Probe (see Table 2). These data support that the primer probes and hybridization probe provide a high degree of specificity and accurate detection of *Cryptococcus neoformans*. No false positives were observed, among the 47 organisms tested.

TABLE 2

| Samples | Results |
|---|---|
| Cocktail 1 - Sample 1 | −* |
| Cocktail 1 - Sample 2 | − |
| Cocktail 2 - Sample 1 | − |
| Cocktail 2 - Sample 2 | − |
| Cocktail 3 - Sample 1 | − |
| Cocktail 3 - Sample 2 | − |
| Cocktail 4 - Sample 1 | − |
| Cocktail 4 - Sample 2 | − |
| Cocktail 5 - Sample 1 | − |
| Cocktail 5 - Sample 2 | − |
| Cocktail 6 - Sample 1 | − |
| Cocktail 6 - Sample 2 | − |
| Cocktail 7 - Sample 1 | − |
| Cocktail 7 - Sample 2 | − |
| Cocktail 8 - Sample 1 | − |
| Cocktail 8 - Sample 2 | − |
| Cocktail 9 - Sample 1 | − |
| Cocktail 9 - Sample 2 | − |
| Cocktail 10 - Sample 1 | − |
| Cocktail 10 - Sample 2 | − |
| Negative Control (no template DNA) | − |
| Positive Control (genomic DNA purified from *Cryptococcus neoformans* ATCC ® No. 2344 at 1:10 dilution) | +** |
| Positive Control (genomic DNA purified from *Cryptococcus neoformans* ATCC ® No. 2344 at 1:100 dilution) | + |
| Positive Control (genomic DNA purified from *Cryptococcus neoformans* ATCC ® No. 2344 at 1:1,000 dilution) | + |

*"−" indicates the absence of PCR amplification in the sample.
**"+" indicates the presence of PCR amplification in the sample.

Example 4

Precision of the PCR Using Primers Directed to the Fungal Specific Transcription Factor in *Cryptococcus neoformans*

To determine the precision of the PCR when using primers directed specifically to the fungal specific transcription factor in *Cryptococcus neoformans*, five (5) technicians were asked to independently conduct the real-time PCR. The study was performed in double-blinded manner, that is, none of the technicians knew the identity of the template DNA in the reaction mixture before and while they were conducting the PCRs.

Each of five (5) technicians independently assessed the precision of the PCR utilizing the combination of the Cneo F1 primer, the Cneo R1 primer, and the Cneo probe by attempting to conduct real-time PCRs using DNA obtained from urine samples, wherein each of nine reaction mixtures was known to be free of DNA of *Cryptococcus neoformans*, and each of nine reaction mixtures was spiked with DNA of *Cryptococcus neoformans* ATCC® No. 2344.

As summarized in Table 3, all five technicians correctly determined which of the eighteen reaction mixtures contained DNA of *Cryptococcus neoformans* and which did not, even though they did not know the identity of the template DNA in each reaction mixture before attempting to conduct the PCRs.

TABLE 3

| Sample | Expected | Technician A | B | C | D | E |
|---|---|---|---|---|---|---|
| 1 | −* | − | − | − | − | − |
| 2 | − | − | − | − | − | − |
| 3 | − | − | − | − | − | − |
| 4 | − | − | − | − | − | − |
| 5 | − | − | − | − | − | − |
| 6 | − | − | − | − | − | − |
| 7 | − | − | − | − | − | − |
| 8 | − | − | − | − | − | − |
| 9 | − | − | − | − | − | − |
| 10 | +** | + | + | + | + | + |
| 11 | + | + | + | + | + | + |
| 12 | + | + | + | + | + | + |
| 13 | + | + | + | + | + | + |
| 14 | + | + | + | + | + | + |
| 15 | + | + | + | + | + | + |
| 16 | + | + | + | + | + | + |
| 17 | + | + | + | + | + | + |
| 18 | + | + | + | + | + | + |
| Negative Control (no template DNA) | − | − | − | − | − | − |
| Positive Control ($1 \times 10^3$ copies of pCneoJE) | + | + | + | + | + | + |
| Positive Control ($1 \times 10^5$ copies of pCneoJE) | + | + | + | + | + | + |
| Positive Control ($1 \times 10^7$ copies of pCneoJE) | + | + | + | + | + | + |

*"−" indicates the absence of DNA of *Cryptococcus neoformans* in the sample.
**"+" indicates the presence of DNA of *Cryptococcus neoformans* in the sample.

Example 5

PCR Using Two (2) Different Set of Primers Directed to the Same Fungal Specific Transcription Factor Gene in *Cryptococcus neoformans*

(a) Nucleotide Sequences for Two (2) Additional Sets of PCR Primers

To further illustrate that primers directed against the fungal specific transcription factor gene is specific for *Cryptococcus neoformans* in a conventional PCR reaction, two (2) additional primer sets (e.g., forward primer, and reverse primer) directed against the same gene in *Cryptococcus neoformans* was prepared. We designed the additional primer sets for the fungal specific transcription factor gene in *Cryptococcus neoformans*. The forward and reverse primers were designed using Beacon Designer 4.02 (Build 402003) (PREMIER Biosoft International, Palo Alto, Calif.). The primer sets having the specified nucleotide sequences were purchased from Integrated DNA Technologies (Stokie, Ill.).

The second primer set contains a second forward primer (Cneo F2) and a second reverse primer (Cneo R2), the nucleotide sequence of which is set forth in Table 4. The third primer set contains a third forward primer (Cneo F3) and a third reverse primer (Cneo R3), the nucleotide sequence of which is set forth in Table 4.

TABLE 4

| Name | Primer sequences | Location | Amplicon Size |
|---|---|---|---|
| Cneo F2 | 5'-TAC AA TCG GTC ACG GTA TT-3' (SEQ ID NO.: 6) | JEC21 Chromosome 9 | 116 bp |
| Cneo R2 | 5'-CTT CGT CTC ATA CCC AGA TC-3' (SEQ ID NO.: 7) | | |
| Cneo F3 | 5'-GGA TGC TTG GAA GGA TCT AT-3' (SEQ ID NO.: 8) | JEC21 Chromosome 9 | 148 bp |
| Cneo R3 | 5'-ATG ACC GTC TAT CCA GTG TA-3' (SEQ ID NO.: 9) | | |

(b) PCR Conditions

Conventional PCR was conducted. In brief, 25 µl containing the extracted DNA (e.g., 500 ng), 600 nM of the second primer set (i.e., Cneo F2 and Cneo R2) (SEQ ID NOs: 6 and 7), and 1×MDL Custom qPCR SuperMix (Quanta BioSciences, Inc., Gaithersburg, Md.). 1×MDL Custom qPCR SuperMix has a Quanta BioSciences catalog number of 172-5008, and the 2× stock solution of the SuperMix contained 50 U/ml of AccuStart™ Taq DNA polymerase, 40 mM Tris-HCl (pH 8.4), 100 mM KCl, 6 mM MgCl$_2$, 400 nM dATP, 400 nM dCTP, 400 nM dGTP, 800 nM dUTP, 40 U/ml of UNG, and proprietary stabilizers of Quanta BioSciences, Inc. The reaction mixture was monitored by gel electrophoresis (ethidium bromide staining) of the amplicon resulting from each successful PCR.

We examined if the second primer set (i.e., the Cneo F2 primer and the Cneo R2 primer) provides a successful amplification product for *Cryptococcus neoformans* (neat) and a concentration range of 1:10 and 1:100 dilutions of *Cryptococcus neoformans* (i.e., extract DNA from ATCC 2344). (lanes 1-4, FIG. 4).

Similarly, we examined if the third primer set (i.e., the Cneo F3 primer and the Cneo R3 primer) provides a successful amplification product for *Cryptococcus neoformans* (neat) and a concentration range of 1:10 and 1:100 dilutions of *Cryptococcus neoformans* (i.e., extract DNA from ATCC 2344). (lanes 6-9, FIG. 4).

Figure 4:
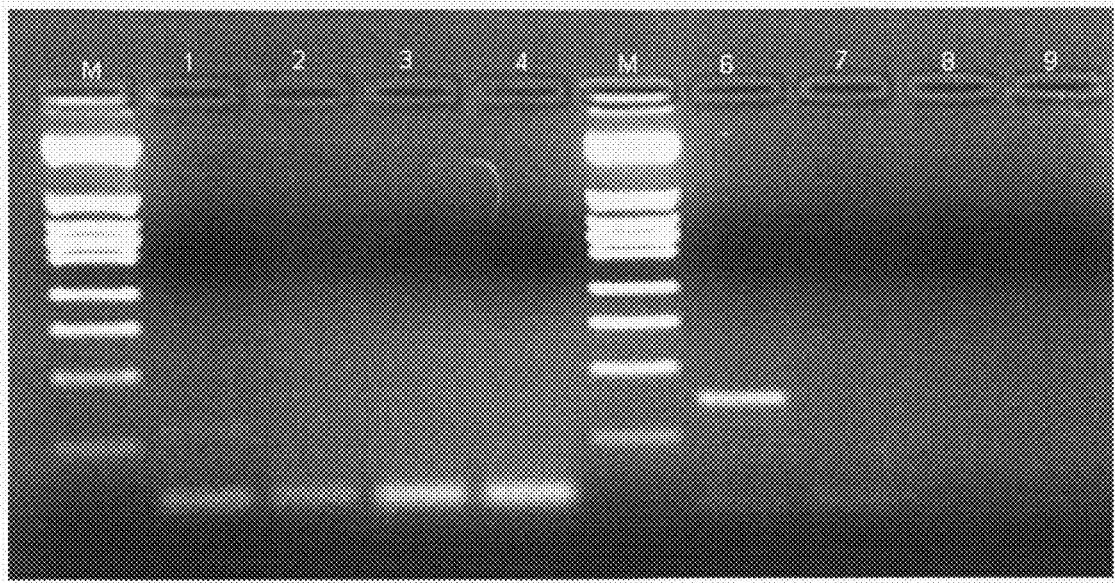
FIG. 4 depicts an ethidium bromide stained DNA gel revealing the amplicon products after conventional PCR amplification of *Cryptococcus neoformans* fungal specific transcription factor gene using the primer sets of SEQ ID NOs: 6 and 7 (Cneo F2 and Cneo R2, respectively) and SEQ ID NOs: 8 and 9 (Cneo F3 and Cneo R3, respectively).

As shown in FIG. 4, both the second primer set and the third primer set produce an amplicon products (size of 116 bp and 148 bp, respectively) (see lanes 1 and 6, FIG. 4). This result indicates that the fungal specific transcription factor gene is specific for *Cryptococcus neoformans*.

Based on these data, it is concluded that primer sets directed against the fungal specific transcription factor gene of *Cryptococcus neoformans* provide a specific PCR tool to detect *Cryptococcus neoformans*. The primers provide specific amplification of an amplicon product for *Cryptococcus neoformans* and not other related species.

Example 6

Percent Identity (% Sequence Identity) Studies

One skilled in the art would appreciate that about 99%, 95%, and 90% sequence identity would behave the same as that of 100% with respect to the ability to anneal to a target DNA and initiate a PCR reaction. In this study, we set out to determine if 80% or less sequence identity may behave as that of 100%. A primer set against the fungal specific transcription factor gene of *Cryptococcus neoformans* was synthesized, which has 80% identity to SEQ ID NOs: 3 and 4 (i.e., the forward primer is 80% identical to SEQ ID NO: 3 and the reverse primer is 80% identical to SEQ ID NO: 4, respectively). (see Table 5).

TABLE 5

| Primers | Sequences | PCR Results |
|---|---|---|
| 100% Identity to Cneo F1 | 5'-GAC ATC GAT CTG CCA TAC TCA TCG-3' (SEQ ID NO.: 3) | +* |
| 100% Identity to Cneo R1 | 5'-GCG TCA CAC TAC AGG TCA GTT G-3' (SEQ ID NO.: 4) | |
| 80% Identity to Cneo F1 (i.e., Cneo F4) | 5'-GAC ATC GAT CTG CCA TAC T-3' (SEQ ID NO.: 10) | -** |
| 80% Identity to Cneo R1 (i.e., Cneo R4) | 5'-GCG TCA CAC TAC AGG TC-3' (SEQ ID NO.: 11) | |

*+indicates the a presence of PCR amplification in the sample
**-indicates the absence of PCR amplification in the sample.

As shown in Table 5, the primer set (i.e., Cneo F4 and Cneo R4) having 80% sequence identity to the first primer set (SEQ ID NOs. 3 and 4) did not provide any PCR amplicon, indicating that the 80% identity primer set is not sufficient to anneal to the template nucleic acid during the real-time PCR, and thus account for the absence of PCR reaction. This result suggests that at least greater than 80% sequence identity is required.

Example 7

Lack of Specificity of the PCR: Using Primers Against Two Another Genes in *Cryptococcus neoformans*

To illustrate the specificity of the fungal specific transcription factor gene in the PCR reaction, we further designed primer sets directed against two different genes. One primer set is against *Cryptococcus neoformans* var. *neoformans* JEC21 chromosome 2, the full length nucleotide sequence is set forth in GeneBank Accession No. AE017342. Another primer set is against *Cryptococcus neoformans* var. *grubii* strain H99 anti-phagocytic protein 1, the full length nucleotide sequence is set forth in GeneBank Accession No. AY965856.

The *Cryptococcus neoformans* var. *neoformans* JEC21 chromosome 2 contains 1,632,307 nucleotides. The *Cryptococcus neoformans* var. *grubii* strain H99 anti-phagocytic protein 1 gene contains 574 nucleotides.

In one study, the primer set was against the *Cryptococcus neoformans* JEC21 chromosome 2 and has the nucleotide sequences as set forth in Table 6 (i.e., SEQ ID NOs: 12, 13 and 14). The primer set was synthesized and used in a real-time PCR with conditions described in Example 1.

In another study, the primer set was against the *Cryptococcus neoformans grubii* strain H99 anti-phagocytic protein and has the nucleotide sequences as set forth in Table 6 (i.e., SEQ ID NOs: 15, 16 and 17). The primer set was synthesized and also used in a real-time PCR with conditions described in Example 1.

TABLE 6

| Name | Gene Location | Base Pair | Sequences |
|---|---|---|---|
| Cneo F5 | *Cryptococcus neoformans* var. *neoformans* JEC21 Chromosome 2 | 116 bp | 5'-CGT TAT GAA GCT TCA AAT CC-3' (SEQ ID NO.: 12) |
| Cneo R5 | | | 5'-TTA CTC GTT CAG TCA TAT ATG-3' (SEQ ID NO.: 13) |

TABLE 6-continued

| Name | Gene Location | Base Pair | Sequences |
|---|---|---|---|
| Cneo Probe 5 | | | 5'/56-FAM/AGG CGA TAG CAG AAC CAC AAC/3BHQ_1/-3' (SEQ ID NO.: 14) |
| Cneo F6 | *Cryptococcus neoformans* var. *grubii* strain H99 anti-phagocytic protein 1 | 131 bp | 5'-CAA CCC AAC AAA TAA TAC ATG-3' (SEQ ID NO.: 15) |
| Cneo R6 | | | 5'-GTT AGC CTT TCT AAG ATC TC-3' (SEQ ID NO.: 16) |
| Cneo Probe 6 | | | 5'/56-FAM/TCC TCT GCC ACT GCT GAA CT/3BHQ_1/ (SEQ ID NO.: 17) |

As shown in the following Table 7, the forward primer (Cneo F1), reverse primer (Cneo R1) and hybridization probe (Cneo probe) successfully detect the presence of *Cryptococcus neoformans*. This serves as the positive control and illustrates that the real-time PCR system was adequate and operational. Fluorescence detection goes as low as 1:100,000 dilutions, indicating that the PCR assay is highly sensitive.

However, the primer set # 5 (i.e., Ceno F5, Cneo R5 and Cneo Probe 5) failed to detect the presence of *Cryptococcus neoformans* in real-time PCR, at the tested dilution ranges of 1:10 to 1:10,000. (see Table 7). Similarly, the primer set # 6 (i.e., Ceno F6, Cneo R6 and Cneo Probe 6) also failed to detect the *Cryptococcus neoformans*. Unlike the fungal specific transcription factor gene, prime sets against two other genes (i.e., *Cryptococcus neoformans* var. *neoformans* JEC21 chromosome 2 and *Cryptococcus neoformans* var. *grubii* strain H99 anti-phagocytic protein 1) both fail to serve as specific markers for *Cryptococcus neoformans*.

TABLE 7

| Sample Nos. | Samples | Results |
|---|---|---|
| | Forward Primer: Cneo F5 (SEQ ID NO.: 12) | |
| | Reverse Primer: Cneo R5 (SEQ ID NO.: 13) | |
| | Hybridization Probe: Cneo Probe 5 (SEQ ID NO.: 14) | |
| 1 | *C. neoformans* (1:10) | −** |
| 2 | *C. neoformans* (1:100) | − |
| 3 | *C. neoformans* (1:1,000) | − |
| 4 | *C. neoformans* (1:10,000) | − |
| 5 | NTC | − |
| 6 | NTC | − |
| | Forward Primer: Cneo F6 (SEQ ID NO.: 15) | |
| | Reverse Primer: Cneo R6 (SEQ ID NO.: 16) | |
| | Hybridization Probe: Cneo Probe 6 (SEQ ID NO.: 17) | |
| 7 | *C. neoformans* (1:10) | − |
| 8 | *C. neoformans* (1:100) | − |

TABLE 7-continued

| Sample Nos. | Samples | Results |
|---|---|---|
| 9 | *C. neoformans* (1:1,000) | − |
| 10 | *C. neoformans* (1:10,000) | − |
| 11 | NTC | − |
| 12 | NTC | − |
| | Forward Primer: Cneo F1 (SEQ ID NO.: 3) | |
| | Reverse Primer: Cneo R1 (SEQ ID NO.: 4) | |
| | Hybridization Probe: Cneo Probe (SEQ ID NO.: 5) | |
| 13 | *C. neoformans* (1:10) | +* |
| 14 | *C. neoformans* (1:100) | + |
| 15 | *C. neoformans* (1:1,000) | + |
| 16 | *C. neoformans* (1:10,000) | + |
| 17 | NTC | − |
| 18 | NTC | − |

NTC: negative template control (i.e., no DNA template)
*"+" indicates the presence of PCR amplification in the sample.
**"−" indicates the absence of PCR amplification in the sample.

Figure 5:
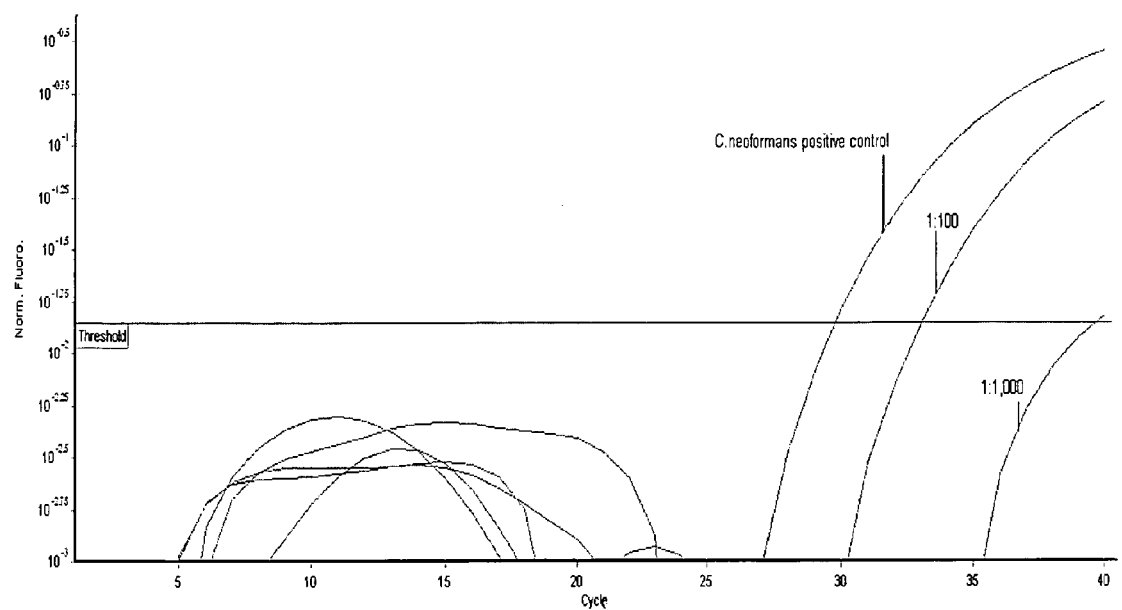
FIG. 5 depicts the detection of the *Cryptococcus neoformans* fungal specific transcription factor gene by Real-Time PCR. Quantitation data displayed (from left to right) are the positive control (i.e., extracted DNA of ATCC® *Cryptococcus neoformans:* 2344) at 1:10, 1:100 and 1:1,000 dilutions. Amplification using primer sets # 5 and 6 (against the *Cryptococcus neoformans* var. neoformanis strain JEC21 chromosome 2 and *Cryptococcus neoformans* var. *grubii* strain H99 anti-phagocytic protein 1, respectively) fail to detect the presence of *Cryptococcus neoformans*.

FIG. 5 depicts fluorescence emitted in an exemplary real-time PCR reaction. Positive control primer set # 1 (i.e., Cneo F1, Cneo R1, and Cneo probe) was used. Dilution of 1:10, 1:100, and 1:1,000 of extracted DNA of ATCC® 2344 was used. While the primer set # 1 was able to detect the presence of *Cryptococcus neoformans*, both the primer sets # 5 and 6 failed to do so (i.e., fluorescence was below the threshold). (FIG. 5).

Although the invention has been described in example embodiments, additional modifications and variations would be apparent to those skilled in the art. It is therefore to be understood that the inventions herein may be practiced other than as specifically described. Thus, the present embodiments should be considered in all respects as illustrative and not restrictive. Accordingly, it is intended that such changes and modifications fall within the scope of the present invention as defined by the claims appended hereto.

What is claimed is:

1. A method of detecting presence of *Cryptococcus neoformans* in a biological sample, comprising:
  (a) mixing
    (i) DNA extracted from said biological sample,
    (ii) a primer pair comprising a forward primer and a reverse primer that target a fungal specific transcription factor gene of *Cryptococcus neoformans*, and
    (iii) a hybridization probe, in a PCR vessel, wherein said hybridization probe comprises a fluorescent moiety;
  (b) amplifying, in a real-time PCR reaction, under conditions to allow production of an amplicon; and
  (c) detecting a presence or absence of *Cryptococcus neoformans*, by detecting a presence or absence of a fluorescent signal resulting from the formation of said amplicon, wherein the presence of a fluorescent signal is indicative of the presence of *Cryptococcus neoformans*.

2. The method of claim 1, wherein said forward primer consists essentially of nucleotide sequence 1121-1144 set forth in SEQ ID NO: 1, nucleotide sequence 1480-1499, or nucleotide sequence 2105-2124 set forth in SEQ ID NO: 1, said reverse primer consists essentially of nucleotide sequence 1512-1533 set forth in SEQ ID NO: 2, nucleotide sequence 1165-1184, or nucleotide sequence 508-527 set forth in SEQ ID NO: 2, and said hybridization probe consists essentially of nucleotide sequence 1150-1178 of SEQ ID NO: 1 or nucleotide sequence 1583-1611 of SEQ ID NO: 2.

3. The method of claim 2, wherein said forward primer has at least 99% identity to a nucleotide sequence 1121-1144 set forth in SEQ ID NO: 1, nucleotide sequence 1480-1499 set forth in SEQ ID NO: 1, or nucleotide sequence 2105-2124 set forth in SEQ ID NO: 1, said reverse primer has at least 99% identity to a nucleotide sequence 1512-1533 set forth in SEQ ID NO: 2, nucleotide sequence 1165-1184 set forth in SEQ ID NO: 2, or nucleotide sequence 508-527 set forth in SEQ ID NO: 2, and said hybridization probe has at least 99% identity to a nucleotide sequence 1150-1178 of SEQ ID NO: 1 or nucleotide sequence 1583-1611 of SEQ ID NO: 2.

4. The method of claim 2, wherein said forward primer has at least 95% identity to a nucleotide sequence 1121-1144 set forth in SEQ ID NO: 1, nucleotide sequence 1480-1499 set forth in SEQ ID NO: 1, or nucleotide sequence 2105-2124 set forth in SEQ ID NO: 1, said reverse primer has at least 95% identity to a nucleotide sequence 1512-1533 set forth in SEQ ID NO: 2, nucleotide sequence 1165-1184 set forth in SEQ ID NO: 2, or nucleotide sequence 508-527 set forth in SEQ ID NO: 2, and said hybridization probe has at least 95% identity to a nucleotide sequence 1150-1178 of SEQ ID NO: 1 or nucleotide sequence 1583-1611 of SEQ ID NO: 2.

5. The method of claim 2, wherein said forward primer has at least 90% identity to a nucleotide sequence 1121-1144 set forth in SEQ ID NO: 1, nucleotide sequence 1480-1499 set forth in SEQ ID NO: 1, or nucleotide sequence 2105-2124 set forth in SEQ ID NO: 1, said reverse primer has at least 90% identity to a nucleotide sequence 1512-1533 set forth in SEQ ID NO: 2, nucleotide sequence 1165-1184 set forth in SEQ ID NO: 2, or nucleotide sequence 508-527 set forth in SEQ ID NO: 2, and said hybridization probe has at least 90% identity to a nucleotide sequence 1150-1178 of SEQ ID NO: 1 or nucleotide sequence 1583-1611 of SEQ ID NO: 2.

6. The method of claim 1, wherein said forward primer has a nucleotide sequence selected from the group consisting of SEQ ID NO: 3, SEQ ID NO: 6, SEQ ID NO: 8, and said reverse primer has a nucleotide sequence selected from the group consisting of SEQ ID NO: 4, SEQ ID NO: 7, and SEQ ID NO: 9.

7. The method of claim 1, wherein said fluorescein moiety is 6-carboxy-fluorescein.

8. A method of detecting presence of *Cryptococcus neoformans* in a biological sample, comprising:
  (a) mixing
    (i) DNA extracted from said biological sample, and
    (ii) a primer pair comprising a forward primer and a reverse primer that target a fungal specific transcription factor gene of *Cryptococcus neoformans*;
  (b) amplifying, in a PCR reaction, under conditions to allow production of an amplicon; and
  (c) detecting a presence or absence of *Cryptococcus neoformans* in said sample.

* * * * *

SEQUENCE LISTING

```
<160> NUMBER OF SEQ ID NOS: 17

<210> SEQ ID NO 1
<211> LENGTH: 2760
<212> TYPE: DNA
<213> ORGANISM: Cryptococcus neoformans

<400> SEQUENCE: 1
taacccccta accctctaac ccctaaccc cctaaccccc taacccccta accccctaac      60
cccctaaccc ctaacccct aagttagcga cgaggagtgg aggttgaatg atcttaaaag     120
```

```
gtgtttttta agtagttttt aattcgggta gcatacacga caacccaata agttaaacaa        180
cgcaaacatg caacctctat aaccctcgct cattcaacaa tttcgaggtg ttttggacaa        240
gtagacggtt tgagaagact aagctggaca aaagatgaac attgttagcc agcggcacgt        300
ctcgccagcg tgatggtaaa cttgcttaaa cattaaacat tacaaggatt tcatgtgaaa        360
ctattgtgag gggcaaaaaa gctatcaaat atactctgct ggtctgcatc caaaggccag        420
taattgataa gatcatctgg aagagtgaag accgtatcat cataacctgt ctgacttatg        480
gcttcaaatg caggctgaga atcgagttca ctgtctaatg aggaagcaaa tggcaattca        540
ggaccacttt cgtccgctgg ttttttctgca cgactgacaa cagcaatttt gggcagctgt        600
ggaccgttga tttgtggatt aggctgtggt gcagtgtttg tcctcgctcg agaggggtag        660
gagactgtgg gcgattcgcc ttgaaaaatg tgatggtccg gttttcggtt gtcaaccgtt        720
gactgcatga agagatcgat tcgggcgata tgcttaagaa gccgctcgct gatccctcct        780
ccggggataa aaggagtctc gaggcaggca agtaagtttg cgaatgacaa actgttcggt        840
cagctttgtt aggacaataa gcgcagttgg acagacagga gggcagctta caggatctgg        900
cggatatgaa ggtacgtgct gatggtcaaa ggacccctgca ccacgctccc caaaagactg        960
ccgactgccg atagctgatg aagctataaa ggaaggtggt cagcaacagg tgaagcgctc       1020
gctctgatga aggcaaaccg acgtacgaat ggcgcgctga tcaactgcat gtacgctgtg       1080
ggtatattcg ccagaacatc cagcagctcg cctgcgatct gacatcgatc tgccatactc       1140
atcggctggc aacaagcgat tgccatccga acagcctttc ctctgtcagc aacttgagcc       1200
cggattgcaa aggtatactt tcggcatcaa ctgacctgta gtgtgacgct caaattcgcc       1260
gcttgaaagc tacagacatt gtcgacaaag tcccccgtca atggcttcgt ctccttgaac       1320
accgatggca acgcgtcgta tctatatctg atgactggcc aagactcgct gacggaaagc       1380
gggggacggc cgaatggact tggtagatct ggaggcttat gtgggcggcc ccgttgattt       1440
tgatacgctg cagcatccat tatctcctcc atggcgcggt acaaatcggt cacggtattc       1500 caccctgta tccagttcac ggtatccagc tcgcctacca acgtaggtga aagagataag       1560
gcgtcgtcca gtcggtgatc tgggtatgag acgaagcttt ggcatcttcg atgacggatc       1620
acaccgcccc aaacggatga cgcgaagaca tcgagcgtat atattgacca gtactactcc       1680
gtccgtcacc attttcccca cggaagcaag acatatagat acgcaccaaa cacctcctct       1740
cctgtacttc ccattttcc agccctgcg ccactgtga tcgtcgtga aacgccaatt       1800 gcgccgacat cccatgatac tgcccgagca tgatctgcaa ttggtcgaaa tccccattct       1860
gtatacccaa aatcgccagt aaagctgttg ctctcagatc gtcgaattcc ggtccgctac       1920
ctgaggcgcg cgaggatatg ctggacaaag cggcgcttcg cagaccgtgg acattcgata       1980
ttatcgctat atcggtgatt ccgcttgagt ctgactggct ggaaggtggg gaccagacct       2040
tgagtagctc gctacatgct ccatcgcgca gacgcgctgc tgccacggca cagacggcca       2100
aaacggatgc ttggaaggat ctatcattat cctgacggcg cgccttgacg tgattaatga       2160
aggttggcca gtgaaagaaa caatacctgc ggaacattca gctgatgatc atcagttggg       2220
cagtctacga agttacactg gatagacggt catccggtac acctccgcaa gctgcagggt       2280
ggtgtcaaga tctatgttgt tggtagctat ccattcgctg gtattgcttg ctcgaatgga       2340
agacggagct ggctgtagcg gtgcatttt gggaggagcc tggacagggc attagcaaaa       2400
tgcaacctgg aatgacttct taacccaccc ctcttcttcc ctgaggtcga tcgtacgtgc       2460
atttttgccc ataatcaata cacggctgac atagtggtgg ggcctctgaa ggcgagcact       2520
```

```
gatagactga tcaatcgaga tccacagctc caaatcgata atttcctcac cttattcccg    2580
agtttatggc atctatcgca ggctctctgg atgacatcag tgcagggatc gccggaggat    2640
aacagtaccc actgagaccc gttttctctt ggaacccaac atgattgatc agtcaagtag    2700
agtttaggat aatcatcaaa gatctggtaa taatcggcaa acaaataaga tgtttttttg    2760

<210> SEQ ID NO 2
<211> LENGTH: 2760
<212> TYPE: DNA
<213> ORGANISM: Cryptococcus neoformans

<400> SEQUENCE: 2
caaaaaaaca tcttatttgt ttgccgatta ttaccagatc tttgatgatt atcctaaact      60
ctacttgact gatcaatcat gttgggttcc aagagaaaac gggtctcagt gggtactgtt     120
atcctccggc gatccctgca ctgatgtcat ccagagagcc tgcgatagat gccataaact     180
cgggaataag gtgaggaaat tatcgatttg gagctgtgga tctcgattga tcagtctatc     240
agtgctcgcc ttcagaggcc ccaccactat gtcagccgtg tattgattat gggcaaaaat     300
gcacgtacga tcgacctcag ggaagaagag gggtgggtta agaagtcatt ccaggttgca     360
ttttgctaat gccctgtcca ggctcctccc aaaaatgcac cgctacagcc agctccgtct     420
tccattcgag caagcaatac cagcgaatgg atagctacca acaacataga tcttgacacc     480
accctgcagc ttgcggaggt gtaccggatg accgtctatc cagtgtaact tcgtagactg     540
cccaactgat gatcatcagc tgaatgttcc gcaggtattg tttctttcac tggccaacct     600
tcattaatca cgtcaaggcg cgccgtcagg ataatgatag atccttccaa gcatccgttt     660
tggccgtctg tgccgtggca gcagcgcgtc tgcgcgatgg agcatgtagc gagctactca     720
aggtctggtc cccaccttcc agccagtcag actcaagcgg aatcaccgat atagcgataa     780
tatcgaatgt ccacggtctg cgaagcgccg cttttgtccag catatcctcg cgcgcctcag     840
gtagcggacc ggaattcgac gatctgagag caacagcttt actggcgatt tgggtatac      900 agaatgggga tttcgaccaa ttgcagatca tgctcgggca gtatcatggg atgtcggcgc     960
aattggcgtt tcacgacgag tcacagtggc cgcagggggct ggaaaaatgg gaagtacagg    1020
agaggaggtg tttggtgcgt atctatatgt cttgcttccg tggggaaaat ggtgacggac    1080
ggagtagtac tggtcaatat atacgctcga tgtcttcgcg tcatccgttt ggggcggtgt    1140
gatccgtcat cgaagatgcc aaagcttcgt ctcatacccca gatcaccgac tggacgacgc    1200
cttatctctt tcacctacgt tggtaggcga gctggatacc gtgaactgga tacagggggtg    1260 gaataccgtg accgatttgt accgcgccat ggaggagata atggatgctg cagcgtatca    1320
aaatcaacgg gccgcccccac ataagcctcc agatctacca agtccattcg gccgtccccc    1380
gctttccgtc agcgagtctt ggccagtcat cagatataga tacgacgcgt tgccatcggt    1440
gttcaaggag acgaagccat tgacggggga ctttgtcgac aatgtctgta gctttcaagc    1500
ggcgaatttg agcgtcacac tacaggtcag ttgatgccga aagtatacct ttgcaatccg    1560
ggctcaagtt gctgacagag gaaaggctgt tcggatggca atcgcttgtt gccagccgat    1620
gagtatggca gatcgatgtc agatcgcagg cgagctgctg gatgttctgg cgaatatacc    1680
cacagcgtac atgcagttga tcagcgcgcc attcgtacgt cggtttgcct tcatcagagc    1740
gagcgcttca cctgttgctg accaccttcc tttatagctt catcagctat cggcagtcgg    1800
cagtcttttg gggagcgtgg tgcagggtcc tttgaccatc agcacgtacc ttcatatccg    1860
ccagatcctg taagctgccc tcctgtctgt ccaactgcgc ttattgtcct aacaaagctg    1920
```

```
accgaacagt tgtcattcg caaacttact tgcctgcctc gagactcctt ttatccccgg    1980
aggagggatc agcgagcggc ttcttaagca tatcgcccga atcgatctct tcatgcagtc    2040
aacggttgac aaccgaaaac cggaccatca cattttttcaa ggcgaatcgc ccacagtctc    2100
ctacccctct cgagcgagga caaacactgc accacagcct aatccacaaa tcaacggtcc    2160
acagctgccc aaaattgctg ttgtcagtcg tgcagaaaaa ccagcggacg aaagtggtcc    2220
tgaattgcca tttgcttcct cattagacag taactcgatt tctcagcctg catttgaagc    2280
cataagtcag acaggttatg atgatacggt cttcactctt ccagatgatc ttatcaatta    2340
ctggcctttg gatgcagacc agcagagtat atttgatagc ttttttgccc ctcacaatag    2400
tttcacatga atccttgta atgtttaatg tttaagcaag tttaccatca cgctggcgag    2460
acgtgccgct ggctaacaat gttcatcttt tgtccagctt agtcttctca aaccgtctac    2520
ttgtccaaaa cacctcgaaa ttgttgaatg agcgagggtt atagaggttg catgtttgcg    2580
ttgtttaact tattgggttg tcgtgtatgc tacccgaatt aaaaactact taaaaaacac    2640
cttttaagat cattcaacct ccactcctcg tcgctaactt agggggttag gggttagggg    2700 gttaggggt tagggggtta gggggttagg gggttagggg gttagagggt tagggggtta    2760
```

<210> SEQ ID NO 3
<211> LENGTH: 24
<212> TYPE: DNA
<213> ORGANISM: Cryptococcus neoformans

<400> SEQUENCE: 3
gacatcgatc tgccatactc atcg                                          24

<210> SEQ ID NO 4
<211> LENGTH: 22
<212> TYPE: DNA
<213> ORGANISM: Cryptococcus neoformans

<400> SEQUENCE: 4
gcgtcacact acaggtcagt tg                                            22

<210> SEQ ID NO 5
<211> LENGTH: 29
<212> TYPE: DNA
<213> ORGANISM: Cryptococcus neoformans

<400> SEQUENCE: 5
caacaagcga ttgccatccg aacagcctt                                     29

<210> SEQ ID NO 6
<211> LENGTH: 19
<212> TYPE: DNA
<213> ORGANISM: Cryptococcus neoformans

<400> SEQUENCE: 6
tacaatcggt cacggtatt                                                19

<210> SEQ ID NO 7
<211> LENGTH: 20
<212> TYPE: DNA
<213> ORGANISM: Cryptococcus neoformans

<400> SEQUENCE: 7
cttcgtctca tacccagatc                                               20

<210> SEQ ID NO 8

```
<211> LENGTH: 20
<212> TYPE: DNA
<213> ORGANISM: Cryptococcus neoformans

<400> SEQUENCE: 8
ggatgcttgg aaggatctat                                                 20

<210> SEQ ID NO 9
<211> LENGTH: 20
<212> TYPE: DNA
<213> ORGANISM: Cryptococcus neoformans

<400> SEQUENCE: 9
atgaccgtct atccagtgta                                                 20

<210> SEQ ID NO 10
<211> LENGTH: 19
<212> TYPE: DNA
<213> ORGANISM: Cryptococcus neoformans

<400> SEQUENCE: 10
gacatcgatc tgccatact                                                  19

<210> SEQ ID NO 11
<211> LENGTH: 17
<212> TYPE: DNA
<213> ORGANISM: Cryptococcus neoformans

<400> SEQUENCE: 11
gcgtcacact acaggtc                                                    17

<210> SEQ ID NO 12
<211> LENGTH: 20
<212> TYPE: DNA
<213> ORGANISM: Cryptococcus neoformans

<400> SEQUENCE: 12
cgttatgaag cttcaaatcc                                                 20

<210> SEQ ID NO 13
<211> LENGTH: 21
<212> TYPE: DNA
<213> ORGANISM: Cryptococcus neoformans

<400> SEQUENCE: 13
ttactcgttc agtcatatatg                                                21

<210> SEQ ID NO 14
<211> LENGTH: 21
<212> TYPE: DNA
<213> ORGANISM: Cryptococcus neoformans

<400> SEQUENCE: 14
aggcgatagc agaaccacaac                                                21

<210> SEQ ID NO 15
<211> LENGTH: 21
<212> TYPE: DNA
<213> ORGANISM: Cryptococcus neoformans

<400> SEQUENCE: 15
caacccaaca aataatacatg                                                21

<210> SEQ ID NO 16
```

```
<211> LENGTH: 20
<212> TYPE: DNA
<213> ORGANISM: Cryptococcus neoformans

<400> SEQUENCE: 16 gttagcctttt ctaagatctc                                              20

<210> SEQ ID NO 17
<211> LENGTH: 20
<212> TYPE: DNA
<213> ORGANISM: Cryptococcus neoformans

<400> SEQUENCE: 17
tcctctgcca ctgctgaact                                               20
```